United States Patent
Halligan et al.

(10) Patent No.: US 7,603,240 B2
(45) Date of Patent: Oct. 13, 2009

(54) PEPTIDE IDENTIFICATION

(75) Inventors: Brian D. Halligan, Wauwatosa, WI (US); Edward A. Dratz, Bozeman, MT (US)

(73) Assignee: MCW Research Foundation, Inc., Milwaukee, WI (US)

(*) Notice: Subject to any disclaimer, the term of this patent is extended or adjusted under 35 U.S.C. 154(b) by 131 days.

(21) Appl. No.: 11/038,642

(22) Filed: Jan. 19, 2005

(65) Prior Publication Data

US 2005/0196811 A1     Sep. 8, 2005

Related U.S. Application Data

(60) Provisional application No. 60/537,605, filed on Jan. 20, 2004.

(51) Int. Cl.
 *G06F 19/00* (2006.01)
(52) U.S. Cl. ........................................ 702/20
(58) Field of Classification Search ............ None
See application file for complete search history.

(56) References Cited

U.S. PATENT DOCUMENTS

| | | | |
|---|---|---|---|
| 5,538,897 | A | 7/1996 | Yates, III et al. |
| 6,017,693 | A | 1/2000 | Yates, III et al. |
| 6,393,367 | B1 | 5/2002 | Tang et al. |
| 2002/0046002 | A1 | 4/2002 | Tang et al. |
| 2004/0024543 | A1 | 2/2004 | Zhang et al. |

OTHER PUBLICATIONS

Griffin et al., Rapid Communications in Mass Spectrometry, 1995, vol. 9, p. 1546-1551.*
Kim et al., Bull. Korean Chem. Soc., 2002, vol. 23, No. 2, p. 315-319.*
Cordwell et al., Electrophoresis, 1995, vol. 16, p. 438-443.*
Shaw, Proceedings of the National Academy of Sciences, 1993, vol. 90, p. 5138-5142.*
Robson et al., CABIOS, 1992, vol. 8, No. 3, p. 283-289.*
Role of Accurate Mass Measurement in (+10 ppm) in Protein Identification Strategies Employing MS or MS/MS and Database Searching by Karl R. Clauser, Peter Baker and Alma L. Burlingame, Anal. Chem. 71, 2871-2882, 1999.
Patchwork peptide sequencing: Extraction of sequence information from accurate mass data of peptide tandem mass spectra recorded at high resolution by Andrew Schlosser and Wolf D. Lehmann, Proteomics, 2, 524-533, 2002.
ProMoST (Protein Modification Screening Tool): a web-based tool for mapping protein modifications on two-dimensional gels by Brian D. Halligan, Victor Ruotti, Weihong Jin, Simon N. Twigger and Edward A. Dratz, Nucleic Acid Research 32, W638-W644, 2004.
Peptide Idenfification Using Peptide Amino Acid Attribute Vectors by Brian D. Halligan, Edward A. Dratz, Xin Feng, Simon N. Twigger, Peter J. Tonellato and Andrew S. Green, Journal of Proteome Research 3, 813-820, 2004.

(Continued)

*Primary Examiner*—John S Brusca
*Assistant Examiner*—Pablo Whaley
(74) *Attorney, Agent, or Firm*—Quarles & Brady, LLP

(57) ABSTRACT

The present invention provides a peptide identification method along with related peptide databases, method of generating the databases, computer usable media, and computer program products. The peptide identification method involves the use of qualitative amino acid composition or partial qualitative amino acid composition information of a query peptide obtained by mass spectrometry to correlate the query peptide to one or more peptides with defined amino acid sequences in a peptide database generated according to the present invention.

20 Claims, 13 Drawing Sheets

```
            L Q
    C Y I K H F R V W E P T N M D A S G
    0 0 1 0 1 0 1 0 1 0 1 0 0 0 1 0 1 1

A.A.C. SCORE = 001010101010001011 = 43659 (decimal)
```

Extended Abstract for the American Society for Mass Spectrometry meeting in Nashville, TN May 23, 2004 by Brian D. Halligan, Andrew S. Greene, Edward A. Dratz., p. 1-2.

Abstract for the American Society for Mass Spectrometry meeting in Nashville, TN May 2004 by Brian D. Halligan, Andrew S. Greene, Edward A. Dratz.

Extended Abstract for the American Society for Mass Spectrometry meeting in Nashville, TN May 23, 2004 by Brian D. Halligan, Andrew S. Greene, Edward A. Dratz.

* cited by examiner

```
            L Q
   C Y I K H F R V W E P T N M D A S G
   0 0 1 0 1 0 1 0 1 0 1 0 0 0 1 0 1 1

A.A.C. SCORE = 001010101010001011 = 43659 (decimal)
```

PEPTIDE IDENTIFICATION

CROSS-REFERENCE TO RELATED APPLICATIONS

This application claims the benefit of U.S. provisional application 60/537,605, filed on Jan. 20, 2004, which is incorporated by reference in its entirety.

STATEMENT REGARDING FEDERALLY SPONSORED RESEARCH OR DEVELOPMENT

This invention was made with United States government support awarded by the following agency: NIH-BAA-HL-02-04. The United States has certain rights in this invention.

BACKGROUND OF THE INVENTION

Protein identification technology has applications in many fields. In the field of proteomics, for example, the ability to identify proteins in a cell or tissue sample is essential to the characterization of the expression and post-translational modification of various proteins and the presence and changes of various protein-protein complexes under different physiological conditions. Proteins do most of the work in cells as pumps, motors, enzymes, channels, signal receptors, amplifiers, and gene regulators. One gene from eukaryotic organisms may give rise to several different proteins, due to alternative splicing of components of the gene, and each protein may be subject to a myriad of post-translational modifications that control the activity, cellular localization, and protein-protein interactions of the protein.

Early in the development of proteomics technology, scientists made use of 1-dimensional (1-D) gel electrophoresis to study the components of protein complexes or 2-dimensional (2-D) gel electrophoresis to separate proteins, combined with subsequent mass spectrometry (MS) to identify proteins via the peptides released from the proteins using specific digestion methods. More recently, experimental approaches have also utilized a combination of liquid chromatography paired with mass spectroscopy (LC-MS). Both the gel approach and LC-MS have allowed the generation of large volumes of MS data that contain information to identify proteins, post-translational modifications thereof, and the members of protein-protein complexes.

Currently, there are several ways to use MS data to identify peptides. One widely used approach is to match the experimental peptide spectra produced by collision induced disassociation (CID) with calculated theoretical spectra of every peptide in a database, such as done by Sequest (Eng, J. K. et al., *J. Am. Soc. Mass Spectrom.* 5:976-989, 1994). Other methods such as the Mascot program (Perkins, D. N. et al., *Electrophoresis* 20:3551-3567, 1999), the Profound program (Zhang, W. and B. T. Chait, *Anal Chem.* 72:2482-2489, 2000), or ProteinProspector (Clauser, K. R. et al., *Analytical Chemistry* 71:2871-2882, 1999) take somewhat different approaches. The peptide mass fingerprinting mode attempts to match the peptide masses measured from a query protein to those deduced from each protein in an amino acid sequence database. A second mode uses the same approach, but adds additional information such as partial sequence, composition, or observed ions as well as the masses of the peptides generated from the protein. The third mode is a MS/MS spectral matching mode, similar to that used by Sequest. The major drawback of the approaches used by Sequest, Mascot, Profound, ProteinProspector, and similar programs is that they are geared to matching the data pair-wise from a single protein to every protein in a database. This is computationally time consuming and expensive. A modified approach, called Turbo Sequest (Thermo Electron, San Jose, Calif.) speeds up the process by creating a mass index to limit the range of peptides searched. However, this latter method has limitations in studies of proteins with post-translational modifications.

Mass spectral matching methods require that there be a match or a near match between an experimental spectrum and a wide range of theoretical spectra generated from a database. This spectral matching is a computationally demanding approach that requires a large number of pair-wise comparisons, each of which involves a large number of calculations. Many of these approaches also depend on the absolute masses of the ions in the MS/MS spectra. This means that the addition of any modification to a peptide causes the masses of many of the ion peaks to change and it is necessary to consider the effects of each possible modification on the theoretical spectra in order to match the shifted experimental peaks to the theoretical spectra of the modified peptide. Since the number of potential modification sites is large, there is a combinatorial explosion of possibilities and it is not practical to generate theoretical spectra from amino acid databases with all possible modifications. An approach to improve spectral matching of modified proteins has been taken by Pevzner and co-workers (Pevzner, P. A. et al., *Genome Research* 11:290-299, 2001). By measuring the deviations between the experimental and theoretical spectral peaks, it is possible to adjust the algorithm for singly modified peptides. However, if the peptide has more than one modification, this method also becomes impractical.

More effective methods for using mass spectral data to rapidly identify peptides and assign peptides to proteins are needed in the art.

BRIEF SUMMARY OF THE INVENTION

In one aspect, the present invention relates to a method for correlating a query peptide to a predicted peptide in a predicted peptide database wherein the query peptide is obtained by cleaving a protein with one or more cleaving agents having defined cleavage specificity so that the cleavage products can be predicted and wherein the predicted peptide database comprises peptides predicted to be generated if said one or more cleaving agents are used to cleave one, two or more preselected amino acid sequences. The method involves (1) providing one or mass spectra for the query peptide wherein each spectrum comprises masses of members selected from immonium ions, modified immonium ions, fragmented immonium ions, dipeptide ions, fragmented dipeptide ions, tripeptide ions, or fragmented tripeptide ions, (2) determining which amino acid is present in the query peptide from said one or more mass spectra to obtain qualitative amino acid composition information for the query peptide, and (3) correlating the query peptide to a predicted peptide in the predicted peptide database based on the qualitative amino acid composition information. Preferably, the correlating step is performed by a computer. Also preferably, the predicted peptide database is generated prior to and independent of any mass spectrum data acquisition for a particular analysis and the predicted peptide database can thus be precomputed, reused, and distributed.

In another aspect, the present invention relates to a method for identifying one or more proteins in a sample containing at least one protein. The method involves cleaving the protein or proteins in the sample with one or more cleaving agents having defined cleaving specificity to generate query peptides, correlating one or more query peptides to one or more predicted peptides in a predicted peptide database as described above, and correlating said one or more predicted peptides to their parent protein or proteins.

In another aspect, the present invention relates to a method for generating a predicted peptide database. The method involves obtaining a plurality of amino acid sequences, predicting what peptides will be generated if each of the amino acid sequences is cleaved by one or more particular cleaving agents having defined cleavage specificity, and storing the resultant peptide information to form a predicted peptide database. In a preferred embodiment, the predicted peptide database is generated by a computer. The predicted peptide database as generated above is also within the scope of the present invention. In one embodiment, the database is stored in a computer usable medium.

In another aspect, the present invention relates to a computer usable medium for generating a predicted peptide database. The medium comprises a means for predicting what peptides will be generated if a protein with a known amino acid sequence is cleaved by one or more cleaving agents having defined cleavage specificity, a means for qualitatively determining the amino acid composition of each resultant peptide, and optionally a means for assigning an amino acid composition score to each of the resultant peptides wherein the amino acid composition score is unique to the corresponding amino acid composition.

In another aspect, the present invention relates to a computer program product comprising a computer usable medium having computer readable program code means embodied in said medium for generating a predicted peptide database, said computer program product including computer readable program code means for causing a computer to predict what peptides will be generated if a protein with a known amino acid sequence is cleaved by one or more cleaving agents having defined cleavage specificity, computer readable program code means for causing a computer to qualitatively determine the amino acid composition for each resultant peptide, and optionally computer readable program code means for causing a computer to assign an amino acid composition score to each of the resultant peptides wherein the amino acid composition score is unique to the corresponding amino acid composition.

DETAILED DESCRIPTION OF THE INVENTION

Figures 1, 2:
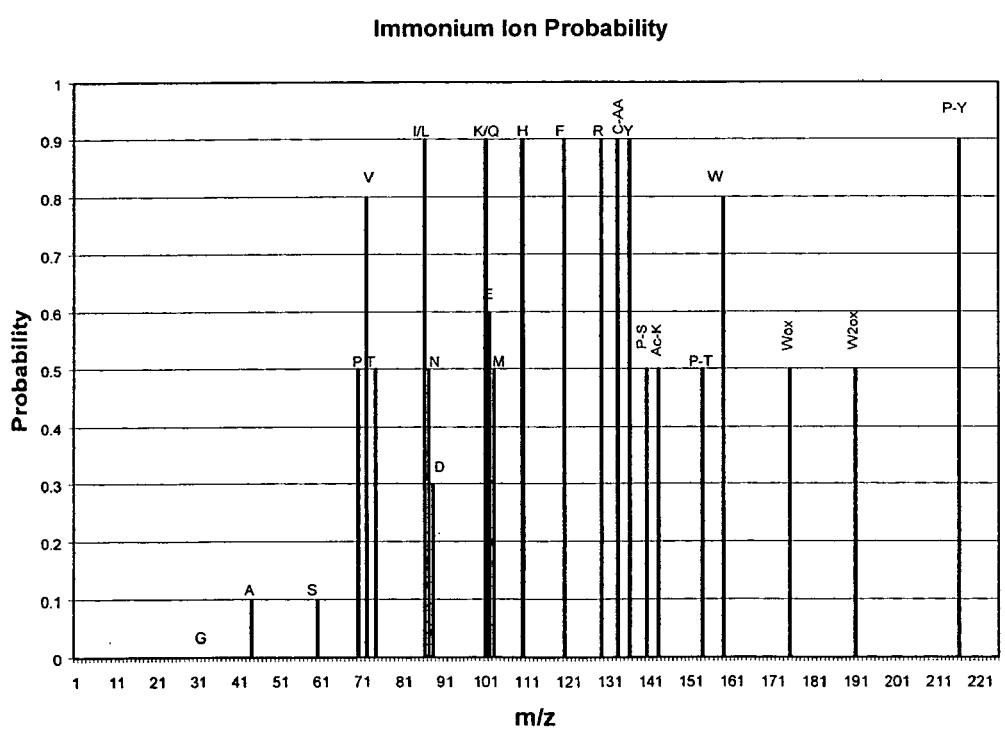
FIG. 1 is an example of assigning a binary amino acid composition (A.A.C.) score to the rat DNM1_RAT (DNA methyltransferase I) peptide HIPLSPGSDWR.
FIG. 2 shows a predicted immonium ion spectrum for peptides containing selected modified and unmodified amino acids. The heights of the bars in the stick spectrum are proportional to the probable intensity of each immonium ion. The cysteine side chain has been alkylated with iodoacetamide (C-AA), but other alkylating groups or cysteine modifications can be used to stabilize the cysteine. Many other modifications are possible, including oxidized W (Wox), doubly oxidized W (W2ox), and acetylated lysine (Ac-K). P-Y is the immonium ion that results from phosphotyrosine. The probable signal intensities of phosphorylated Ser (P-S) and phosphorylated Thr (P-T) immonium ions can be increased by beta elimination of the phosphate and reaction with a suitable thiol-containing reagent. The probable intensities of the D and E immonium ions can be increased by methylation.

The present invention provides a peptide identification method along with related peptide databases, method of generating the databases, computer usable media, and computer program products. The peptide identification method involves the use of qualitative amino acid composition or partial qualitative amino acid composition information of a query peptide obtained by MS to correlate the query peptide to one or more peptides with defined amino acid sequences in a peptide database generated according to the present invention. "Qualitative amino acid composition" is defined as the presence or absence of amino acids in a peptide, irrespective of the total number of each type of amino acid. The molecular mass information of a query peptide and peptides in the database can also used in the method of the present invention to assist the identification of the query peptide. Unlike prior art peptide identification methods which require computationally demanding tasks of comparing theoretical and experimental MS patterns of sequence fragments or determining a full or partial sequence of the peptide from MS data, the method of the present invention involves relatively simple computations and thus requires less computation resources.

The example below demonstrates that the peptide identification method of the present invention is as accurate as identification based on complete peptide amino acid sequence data (see FIGS. 4-6 and related text) and works well on data from large and small genomes (e.g., from human to archaea). The example further demonstrates that the method works well even if one or more amino acids in the query peptide are not detected (see FIG. 5 and related text) and the mass of a query peptide is not known with high accuracy. This is an important advantage as it is extremely difficult to obtain the complete amino acid sequence of a peptide reliably and most prior art methods for peptide identification rely on partial sequence information or a sequence-dependent pattern of partial peptide fragmentation. Furthermore, the method of the present invention typically only requires a relatively low and easily obtainable degree of mass accuracy (e.g., less than 100 ppm) in the mass spectrometer to uniquely identify a query peptide in many cases, as the number of peptides needed to be identified to correlate reliably with a query peptide by the method of present invention is often less than 10.

The peptide identification method can be used, for example, to identify one or more proteins in a protein sample. The proteins in the sample are first cleaved with one or more cleaving agents to generate constituent peptides and the constituent peptides are correlated to peptides of known protein origin in a peptide database according to the present invention. The proteins in the sample can therefore be identified by tracing them to known proteins.

Protein Cleavage

Query proteins are cleaved at predictable amino acid positions to generate query peptides. Any suitable methods and agents known in art can be used. In one embodiment, proteins are cleaved by an enzyme such as trypsin, endoproteinase Asp-N, chymotrypsin, endoproteinase Lys-C, or endoproteinase Arg-C. Trypsin is a preferred enzyme. In another embodiment, proteins are cleaved by a chemical agent such as cyanogen bromide. Various combinations of enzymes and/or chemical agents can also be used. Preferably, peptides of about 9 to about 31 or about 10 to about 30 amino acids are generated as a result of the cleavage.

Mass Spectrum of a Query Peptide

In generating a mass spectrum for a query peptide, the query peptide should be sufficiently fragmented to produce immonium ions. Immonium ions have the general formula of $NH_2^+=CHR$, where R is the amino acid side chain or modified amino acid side chain. Immonium ions can be produced by high-energy cleavage of the amide bond between amino acids in peptides. The masses of the immonium ions are characteristic of the amino acids or the modified amino acids in the peptides, due to the differences in masses of their "R-" groups. Due to the differences in molecular mass, the immonium ions of most amino acids are sufficiently spaced on the spectrum so that their presence can be readily detected. Preferably, a method employed to generate the spectrum also provides information on the molecular mass of a query peptide.

It is noted that other low mass fragments may also be present on the spectrum. For example, certain immonium ions are not stable and tend to break down into specific, more stable lower mass fragments (signature fragments). The presence of a specific signature immonium ion fragment indicates the presence (in the query peptide) of an amino acid that corresponds to the parent immonium ion. Due to incomplete fragmentation of a query peptide, dipeptides and specific breakdown fragments thereof and tripeptides and specific breakdown fragments thereof may also be present. These dipeptides, tripeptides, and break down fragments are specific and can be used to identify amino acids present in the query peptide. If certain amino acids in the query peptide are modified, immonium ions of modified amino acids will also be present. The above immonium ion fragments, dipeptides, dipeptide fragments, tripeptides, tripeptide fragments, and modified immonium ions, along with unmodified immonium ions, are collectively referred to as informative fragments and ions for the purpose of the present invention.

Any known method or system that can generate a mass spectrum for a query peptide as described above can be used in the present invention. Examples ion sources that can be used include but are not limited to electrospray ionization (ESI), matrix assisted laser desorption/ionization (MALDI), and matrix-free surface assisted laser desorption/ionization (SALDI). In one embodiment, the mass spectrum generated is a CID or post source decay (PSD) spectrum.

Conventional MALDI mass spectrometry, using UV-absorbing matrices on metal surfaces and 337 nm or 355 nm UV excitation, produces relatively abundant immonium ions and other informative fragments and ions. Immonium ions and other informative fragments and ions are produced by high energy CID in gas collision cells. The weaker informative fragments and ions can sometimes be lost in the high chemical noise from MALDI matrices in the low mass region (where the immonium ions and other informative fragments and ions occur). Modern MALDI TOF(time of flight)/TOF or MALDI ion traps have less chemical noise but their efficiency for producing immonium ions of target peptides may be lower than conventional MALDI.

Most MALDI samples are prepared on sample-plates made of stainless steel or aluminum. The role of the metal substrate in the desorption/ionization process is not well understood, but the surface conductivity of the metal is often considered important to preserve the integrity of the electrostatic field around the sample during ion ejection. Plastic is the second most common material used as a substrate in MALDI sources. Examples of plastic substrates that can be used include but are not limited to poly(vinylidene fluoride) and poly(ethyleneterephthalate) (Walker, A. K. et al. *Anal. Chem.* 71:268-72, 1999), teflon (Hung, K. C. et al. *Anal. Chem.* 71:518-21, 1999 and Hutchens, W. and T. T. Yip *Rapid Commun. Mass Spectrom.* 7:576-580, 1993), Nafion (DuPont, Wilmington, Del.), polypropylene (Hutchens, W. and T. T. Yip *Rapid Commun. Mass Spectrom.* 7:576-580, 1993), polystyrene (Hutchens, W. and T. T. Yip *Rapid Commun. Mass Spectrom.* 7:576-580, 1993), and nylon (Hutchens, W. and T. T. Yip *Rapid Commun. Mass Spectrom.* 7:576-580, 1993). Glass and ceramics can also be used as substrates in MALDI sources (Hutchens, W. and T. T. Yip *Rapid Commun. Mass Spectrom.* 7:576-580, 1993).

SALDI can produce laser TOF mass spectra with exceedingly low chemical noise, very low background signals, and good sensitivity (Sunner, J. et al. *Anal. Chem.* 67:4335-42, 1995). Examples of materials that can serve as SALDI surfaces include but are not limited to graphite, activated carbon films (Han, M. and J. Sunner *J. Am. Soc. Mass Spectrom.* 11:644-9, 2000), and porous silicon (Shen, Z. et al. *Anal. Chem.* 73:612-9, 2001). SALDI conducted with porous silicon is also referred to as desorption/ionization on porous silicon (DIOS) (Shen, Z. et al. *Anal. Chem.* 73:612-9, 2001). Silicon surfaces with less porosity are less susceptible to surface contamination under practical laboratory conditions in comparison to silicon surfaces of higher porosity (Alimpiev, S. et al. *J. Chem. Phys.* 115:1891-1901, 2001).

Conventional 337 nm, 355 nm, and other similar wavelength UV irradiation at high intensity can be employed in MALDI and SALDI to produce informative fragments and ions. Preferably, to optimize the production of informative fragments and ions with low background, high energy UV laser pulses in the far region such as that of about 157 nm to about 225 nm are employed in MALDI and SALDI. Far UV excitation such as that conducted with the wavelength of 193 nm or 213 nm has been shown in other situations to be very effective in breaking peptide bonds between amino acids in solution (Nikogosyan, D. N. and H. Gomer *Biol. Chem.* 378: 1349-51, 1997; Repeyev, Y. A. et al. *J. Photochem. Photobiol.* B 12:259-74, 1992; Repeyev, Y. A. et al. *J. Photochem. Photobiol.* B 17:89, 1993; and Mulcahy, M. et al. Biol. Chem. 381:1259-62, 2000). In a preferred embodiment of the present invention, far UV excitation is used with SALDI to produce immonium ions and other informative fragments and ions.

In order to determine the qualitative amino acid composition of individual query peptide from its mass spectrum, it is preferred that the peptides generated via the cleavage of query proteins be sufficiently separated from each other before being ionized and fragmented to produce informative fragments and ions. Peptide mixtures can be recognized in MALDI or SALDI by the masses of the parent peptides assessed at lower laser power near the threshold for desorption/ionization, or by ESI. In a preferred embodiment, peptides are separated by liquid chromatography and laid down on MALDI or SALDI plates for ionization and fragmentation. It is noted that limited peptide impurities can be tolerated by using the relative intensities of immonium ions and other informative fragments and ions. The efficiency of peptide cleavage by far UV excitation does not strongly depend on peptide sequence, but the intensities of some immonium ions are typically higher than others. The intensities of the strongest immonium ions in the spectra can be used to predict the relative intensities of the weaker immonium ions, if present. Thus, the intensities of the strongest immonium ions can be used to set a threshold for relevant intensities of the weaker immonium to be considered from the major peptide versus a contaminating or minor peptide.

As an example, we provide below one illustrative approach for processing and analyzing a low complexity sample, a medium complexity sample, and a high complexity sample.

For a low complexity protein sample, such as proteins in 1-D gel bands or 2-D gel spots obtained from protein complexes, the proteins can be digested and the peptides can be separated using 1-D LC effluent to deposit peptide fractions onto SALDI or MALDI plates for analysis or for injection into ESI for analysis.

For a medium complexity protein sample, the proteins can be digested and the peptides can be separated using 2-D LC to resolve most peptides in a purified form and to deposit peptide fractions onto SALDI or MALDI plates or into ESI for analysis.

For a high complexity protein sample, it can be converted to several low complexity protein samples by various prefractionation methods such as 1-D or 2-D protein gels and each of the resultant low complexity samples is then processed and analyzed accordingly.

For situations where it is impractical to purify single peptides, 2-D LC and other more sophisticated LC can be used to separate the peptides to the degree of practically possible and the peptide factions are deposited onto SALDI or MALDI plates or into ESI. One also need to select parent ions in a mass spectrometer out of the peptide mixtures for high energy CID fragment mass analysis to detect immonium ions and other small peptide fragments related to the dipeptide and tripeptide components of the target peptide to arrive at a complete or reasonably complete amino acid composition of the target peptide.

In another embodiment, tandem MS/MS methods are employed to separate various peptides and generate spectra of immonium ions and other informative fragments and ions to obtain information on the amino acid composition of the peptides (such as by higher energy CID of parent ions, followed by ion trap, quadrapole, TOF, or FTMS analysis).

Determination of the Amino Acid Composition of a Query Peptide

Qualitative amino acid composition information of a query peptide can be obtained from a mass spectrum (e.g., a CID or PSD spectrum) described above based on differences between peaks in or from the masses of observed immonium ions and other informative fragments and ions as diagrammed in FIG. 2. The mass list obtained is compared to the known masses of unmodified or modified amino acids to produce a list of amino acids present in the peptide. There is sufficient mass difference between the peaks so that which of the amino acids are present or absent can be determined. The amino acid identification need not be limited to the most prominent ions as other minor species may also be diagnostic. For amino acids that may not produce very abundant immonium ions, their presence may be detected by reference to informative fragments derived from dipeptides and/or tripeptides. The mass of a query peptide and incomplete data on amino acid composition can often be used together to deduce one or more additional amino acids in the composition.

Two of the amino acids, leucine and isoleucine have the same chemical composition and therefore the same mass and very high energy CID or high laser energy is required to produce distinguishable fragmentation products. Similarly, lysine and glutamine are close in molecular mass (128.05858 vs. 128.09497) but the presence of this pair of amino acids can be distinguished by examining their most prominent immonium ions (101.0715 vs. 101.1079, a 364 ppm difference), and the fact that lysine produces an additional major immonium ion species of 84.08136, due to loss of ammonia.

Modified amino acids produce immonium ions of different masses than the unmodified amino acids, as diagrammed in part in FIG. 2. For example, phosphoserine has an immonium ion at 140 amu (80 amu higher than serine) and phosphothreonine has an immonium ion 154 amu. The phosphotyrosine immonium ion occurs at 216.043 amu and with an accompanying neutral loss of 79.97 it also produces a tyrosine immonium ion (Salek, M. et al. *Anal. Chem.* 75:2724-9, 2003). There are other peptide fragments derived from dipeptides and tripeptides that have a similar mass to the phosphotyrosine immonium ion (such as the a2 ion of GW) and it is necessary to either require the presence of a tyrosine ammonium ion to score the phosphotyrosine immonium ion and/or to use a sufficiently high resolution mass spectrometer to distinguish the other possibilities from the authentic phosphotyrosine immonium ion (Steen, H. et al., *J. Mass Spectrom.* 36:782-790, 2001). Acetylated lysine produces two prominent immonium ions; one is the parental ion at 143.1 and the other is a secondary ion at 126.1, due to the loss of ammonia. In some cases derivatives can be formed of modified amino acids that provide a stronger immonium ion signal and a distinctive mass. For example, when phosphoserine and phosphotryrosine are treated with base (e.g. 1 M barium hydroxide), a beta elimination reaction produces dehydroalanine and this can be reacted with sulfhydryl reagents to form stable adducts that give distinctive immonium ions. When these modified amino acid species are encountered in the experimental data, the unmodified amino acid is considered to be present in the underlying parent peptide and the evidence for the modification of the query peptide is recorded.

Generation of Predicted Peptide Database

Figure 3:
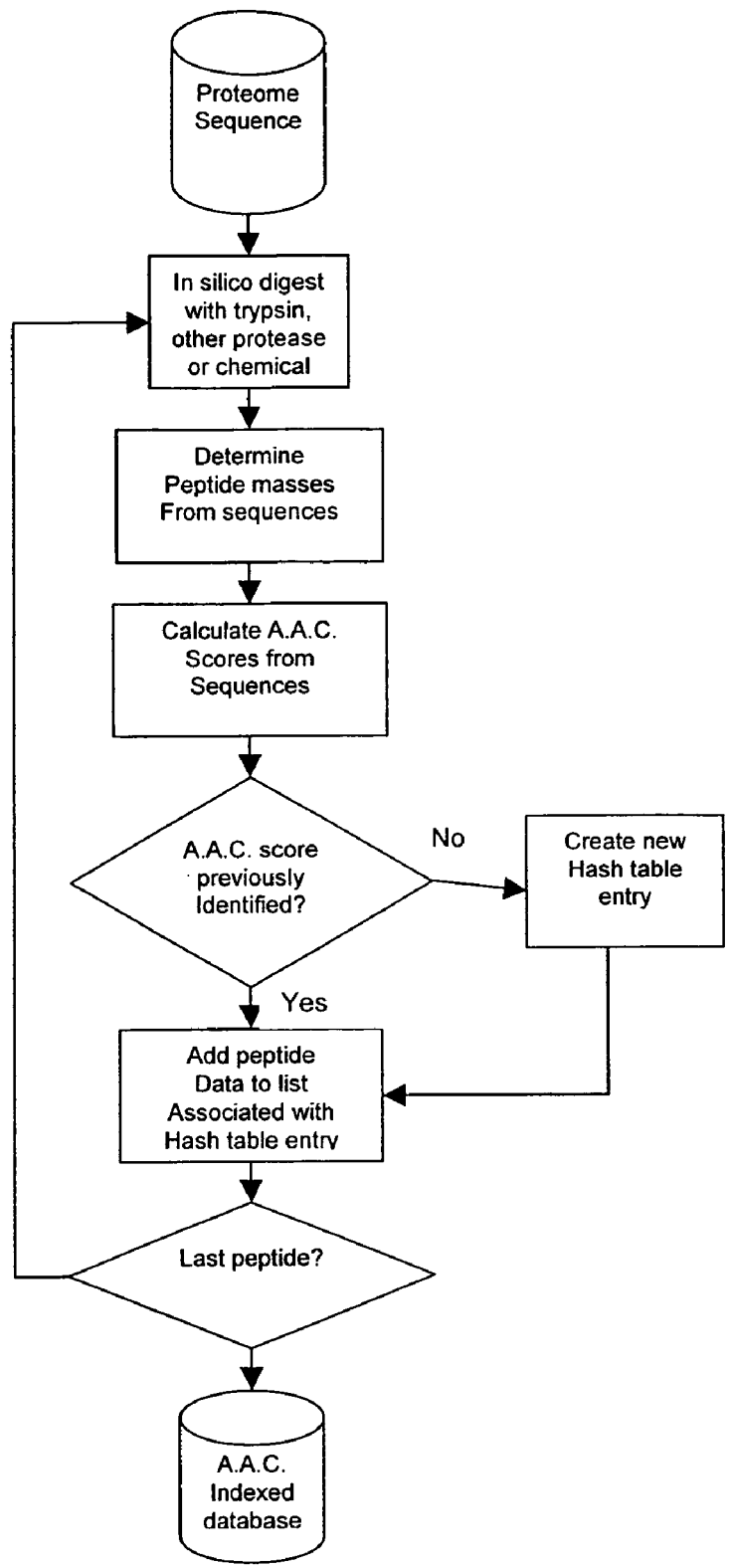
FIG. 3 shows an embodiment for the construction of a predicted peptide database. A.A.C.=amino acid composition.

A predicted peptide database can be derived from any source suitable to a particular application. For example, any collection of amino acid sequence data from proteins or peptides, such as the publicly available databases from NCBI, EMBL, EBI, and DDBJ as well as any other public or private collection of sequence data can be used. Also, any collection of biological data from which amino acid sequence data can be derived or deduced such as, nucleic acid databases, whole genomes, collections of EST sequences, and any other information that can be converted to amino acid sequence data can be used to generate a predicted peptide database. For any nucleotide sequence whose orientation and/or reading frame cannot be definitively established, each of the six possible reading frames is converted into an amino acid sequence. In generating a predicted peptide database, the amino acid sequences of the proteins and peptides are divided into peptides either by a sliding window method or preferably by predicting the cleavage of the amino acid sequences based on the specific cleavage rules defined by one or more particular cleavage agents. It is preferred that the predicted peptide database used for a particular application is generated using the cleavage rules of the same cleavage agent(s) as used in the actual experimentation to obtain query peptides. FIG. 3 illustrates one embodiment for generating a predicted peptide database using the cleavage rules of trypsin. Since protein digestion does not always go to completion under experimental conditions, it is therefore also preferred to include various numbers of missed cleavages, i.e. peptides that contain within them potential cleavage sites, into a predicted peptide database, as well as specific losses of amino acids from the ends of peptides that may be induced by some experimental methods.

The use of a defined specificity of a cleavage agent to divide the amino acid sequences into peptides has some advantages over using sliding windows methods. One advantage is that the use of a defined specificity reduces the total number of peptides by ten fold or greater. A second advantage is that it imposes an internal frame of reference. In this way, it is much more likely that analogous peptides will be compared. A disadvantage with a defined specificity is that mutations or errors that alter the cleavage sites will tend to lead to missed peptides. This problem can be readily addressed by using multiple different cleavage specificity. The probability of the occurrence of homologous peptides with changes in multiple cleavage specificities is low.

Figure 4:
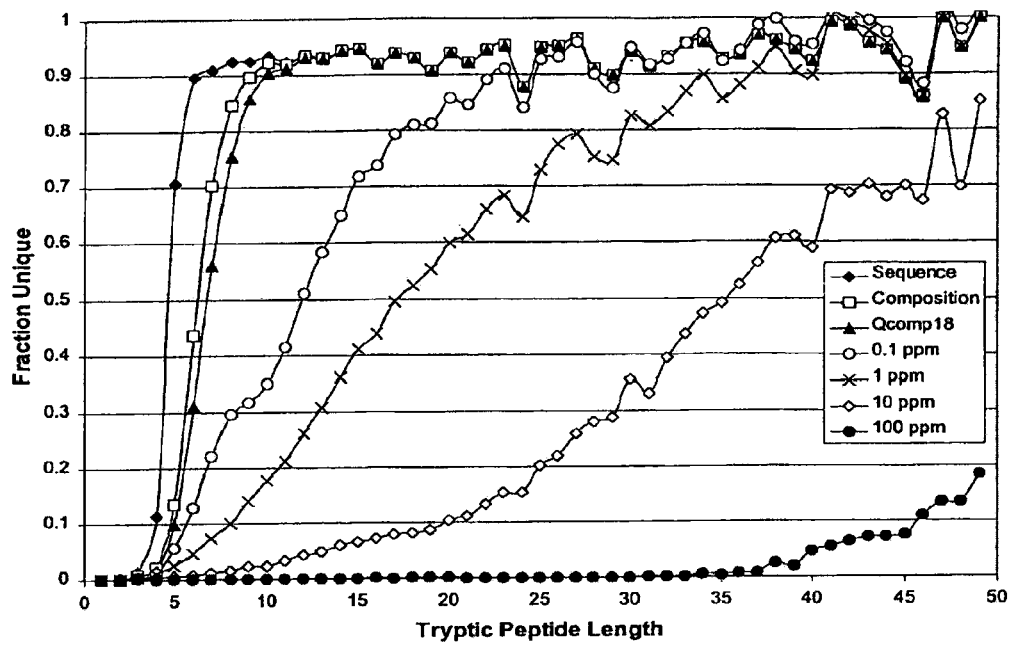
FIG. 4 shows unique tryptic peptides in yeast vs. peptide length. The fraction of tryptic peptides that are unique by sequence was determined from a complete in silico trypsin digestion of the yeast proteome (EBI) and is plotted vs. peptide length (♦). The fraction of tryptic peptides unique by amino acid composition (□—20 amino acids, ▲—18 amino acids) and the fraction of peptides unique by mass at different mass resolutions (0.1 ppm—(○), 1 ppm—(X), 10 ppm—(◇), 100 ppm—●) are also plotted. An analysis of the fraction of peptides unique by mass vs. peptide mass for the yeast proteome was previously published by Smith (Smith, R. D. *International Journal of Mass Spectrometry* 200, 509-544, 2000).
Figure 5:
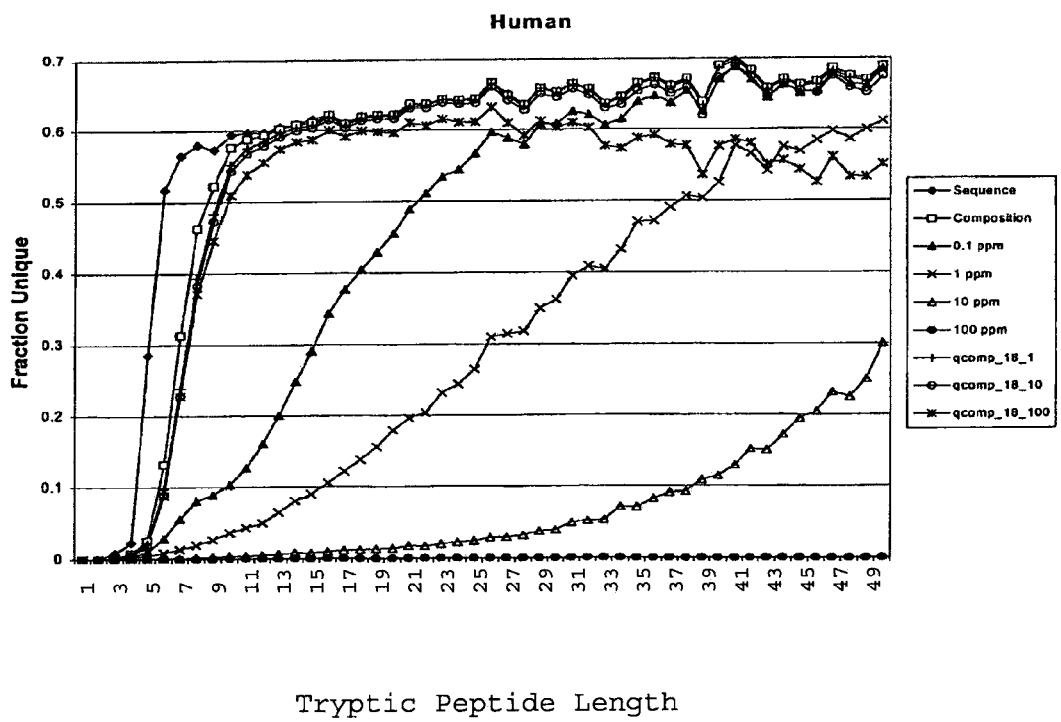
FIG. 5 shows unique tryptic peptides in human vs. peptide length as analyzed in FIG. 4. The data denoted with symbols corresponding to Qcomp_18_1, 10, or 100 refer to classification by Qcomp 18 with further mass discrimination by 1, 10, or 100 ppm mass accuracy.
Figures 6A, 6B:
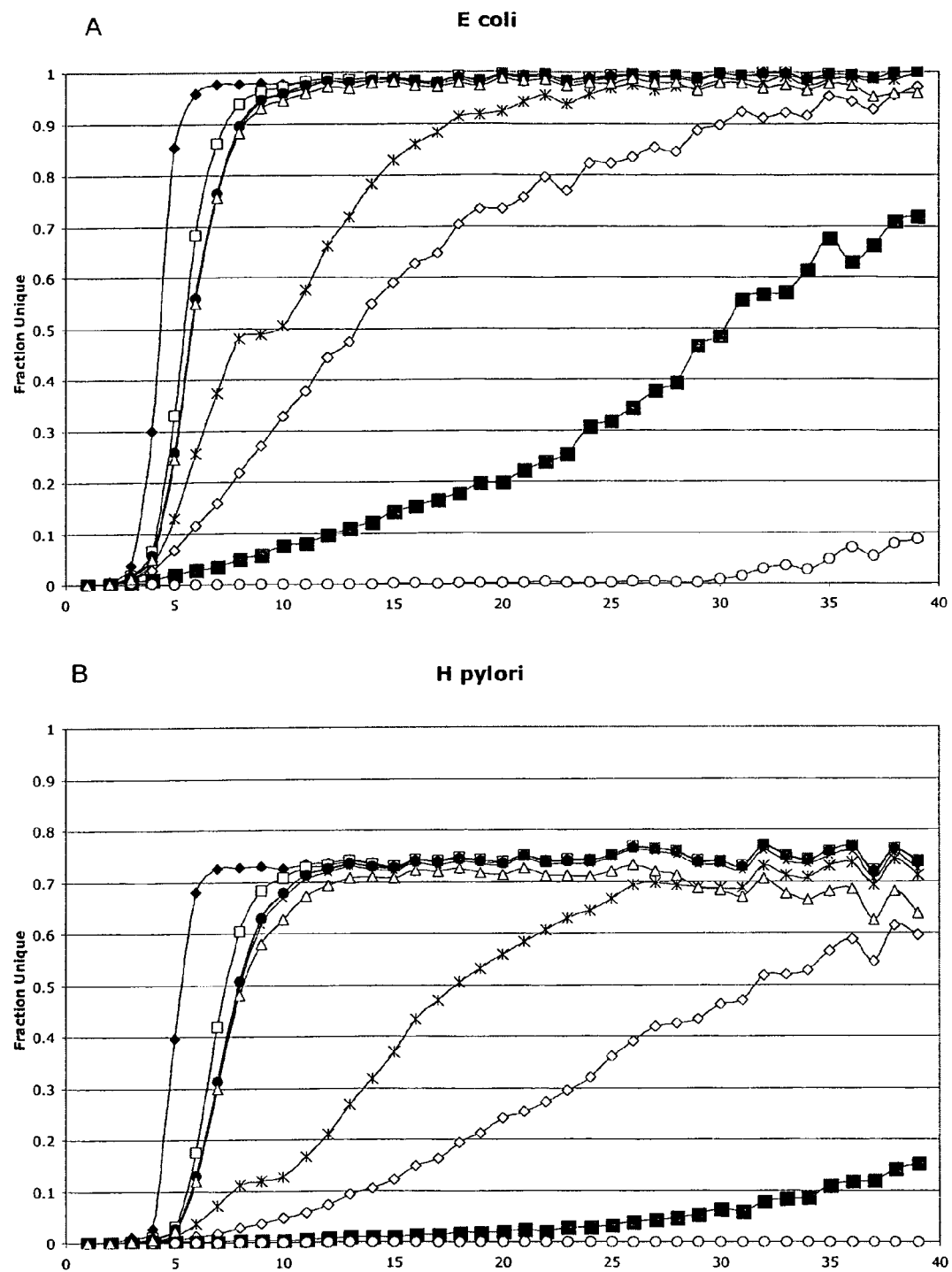
FIG. 6 shows unique tryptic peptides in various other proteomes vs. peptide length as analyzed in FIGS. 4 and 5. Symbols are as indicated in the *M. musculus* key.
Figures 6C, 6D:
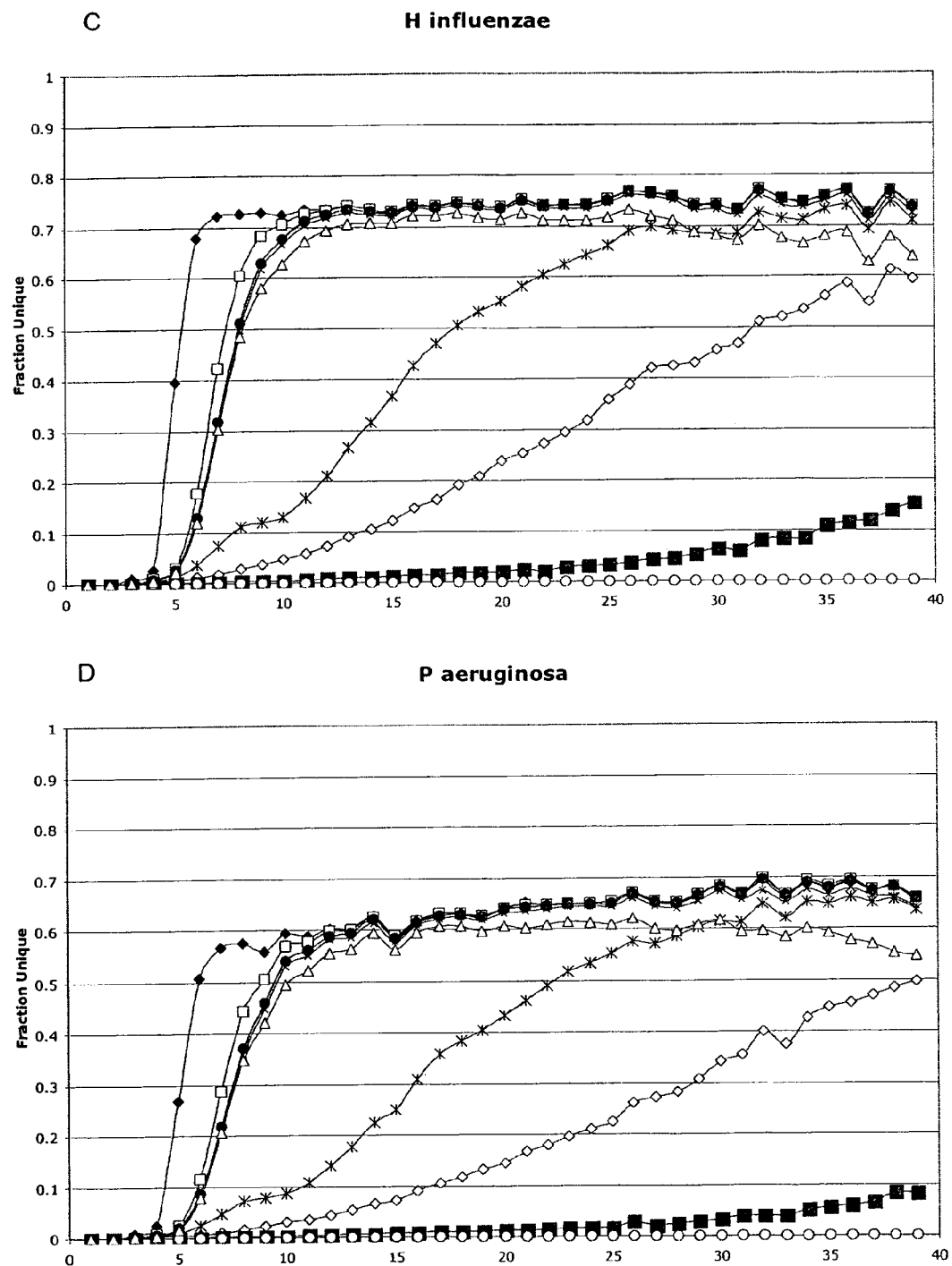
Figure 6E:
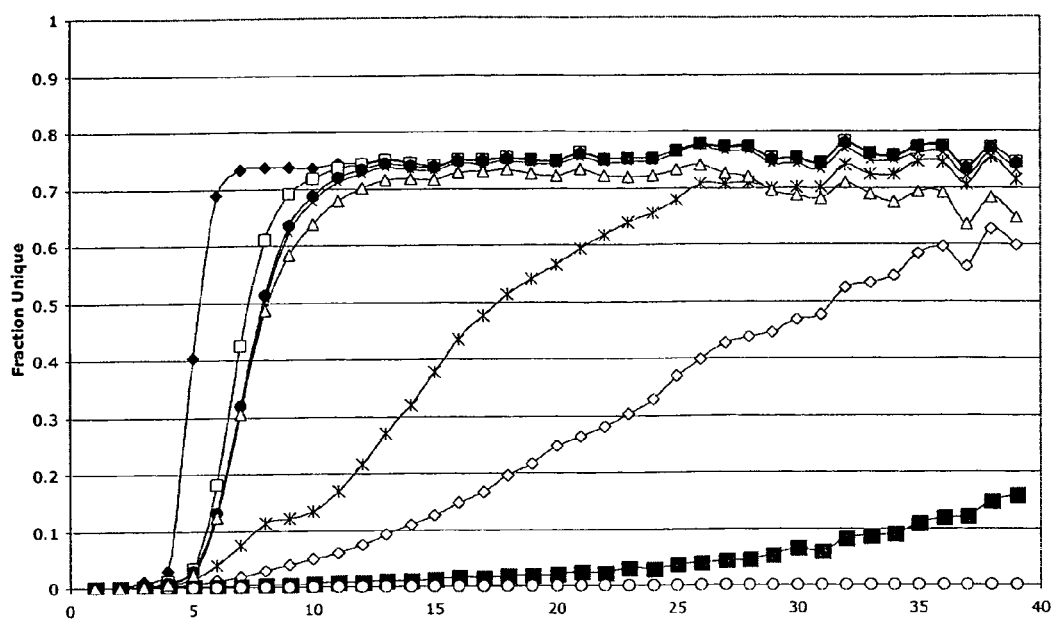
Figure 6F:
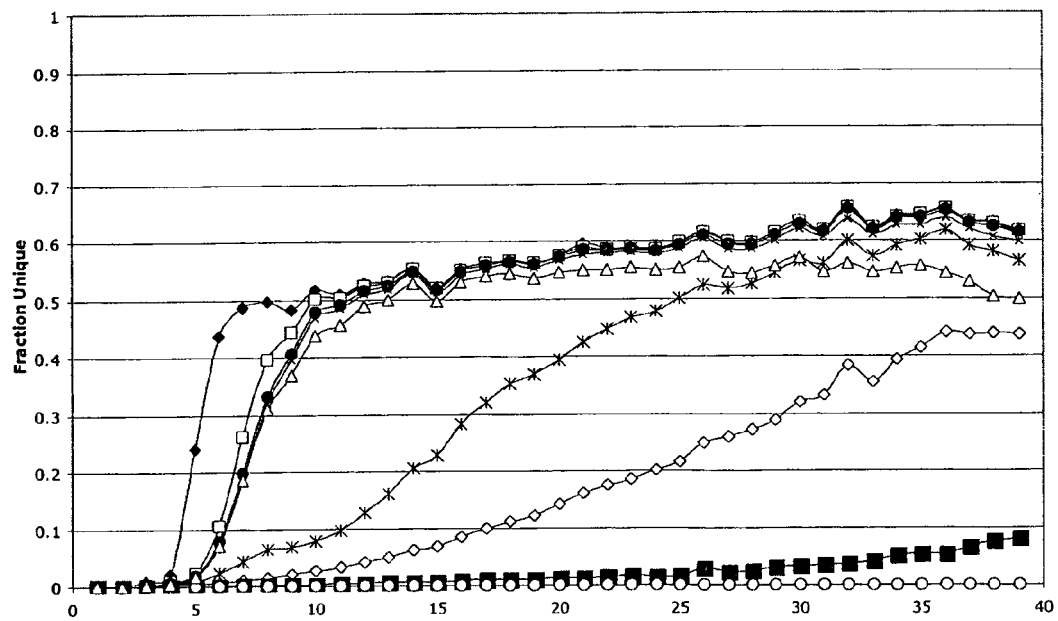
Figures 6G, 6H:
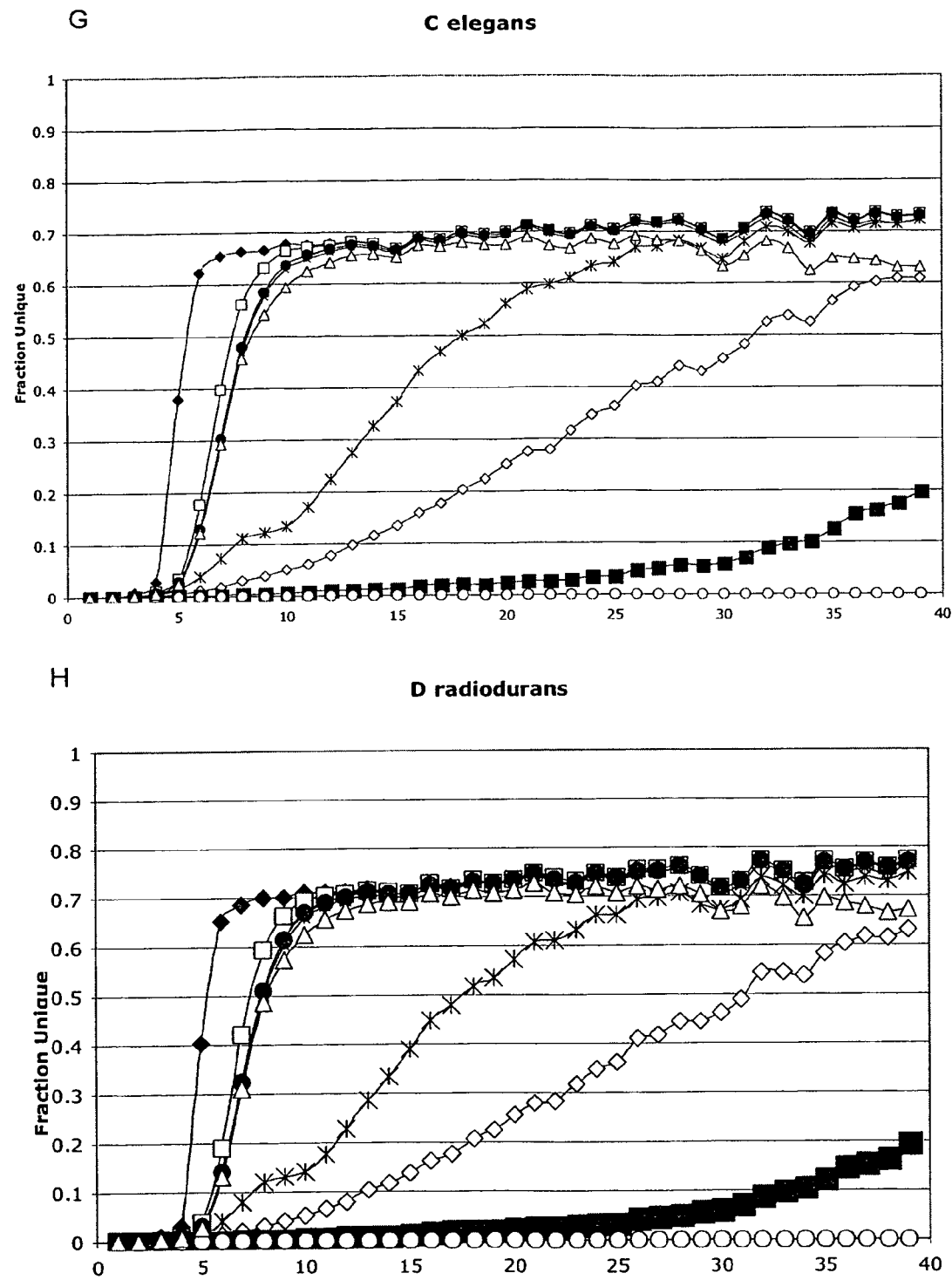
Figure 6I:
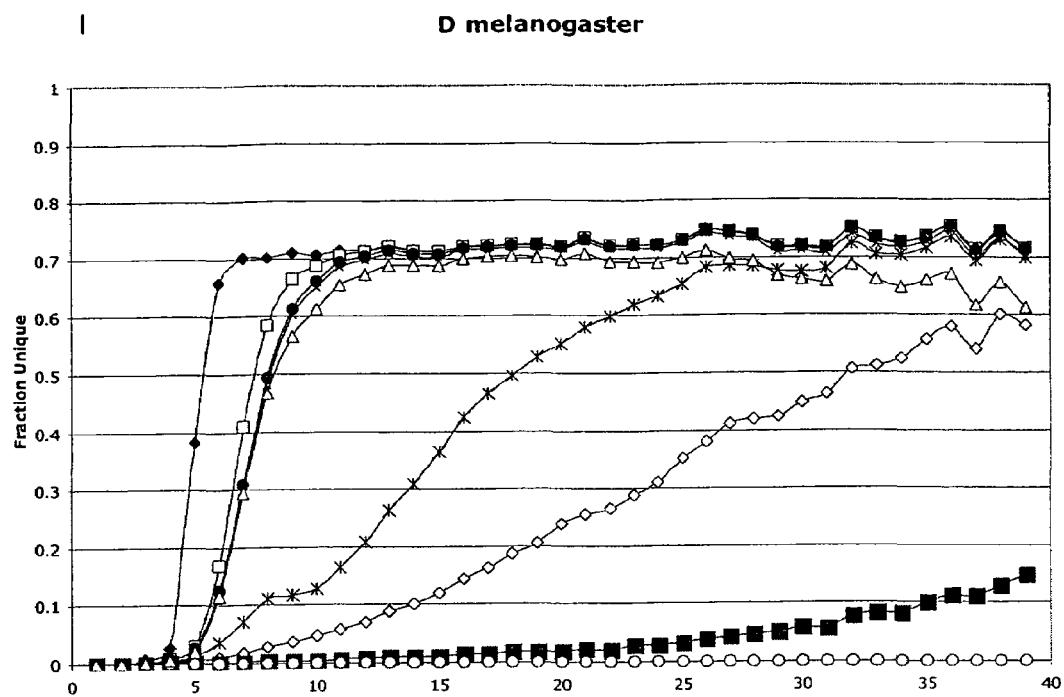
Figure 6J:
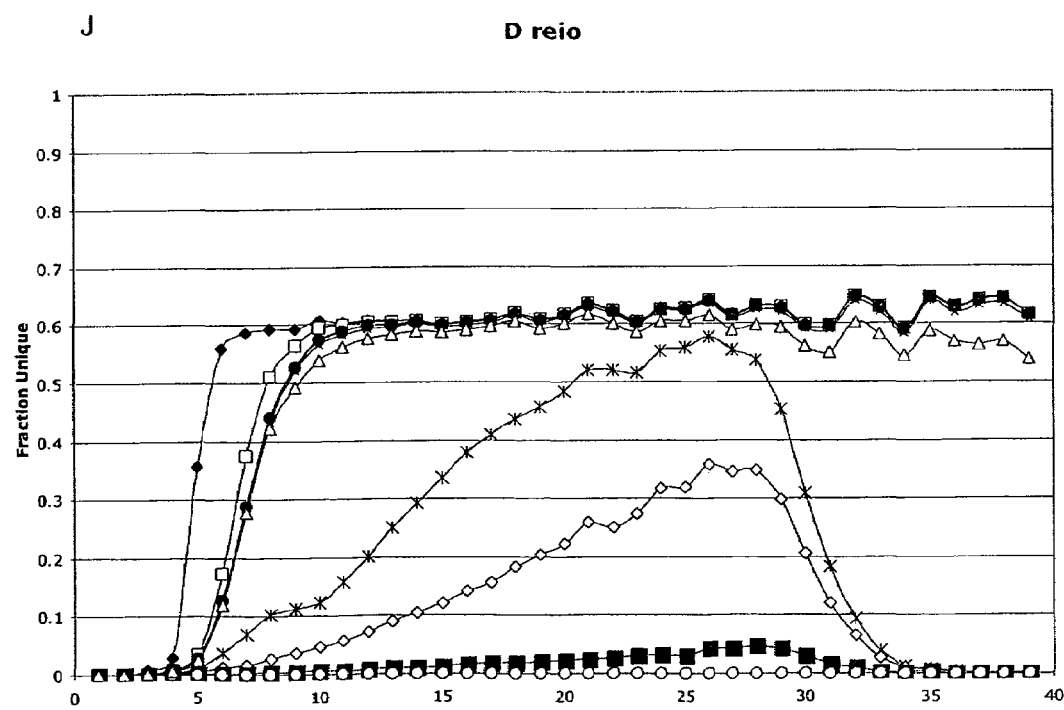
Figure 6K:
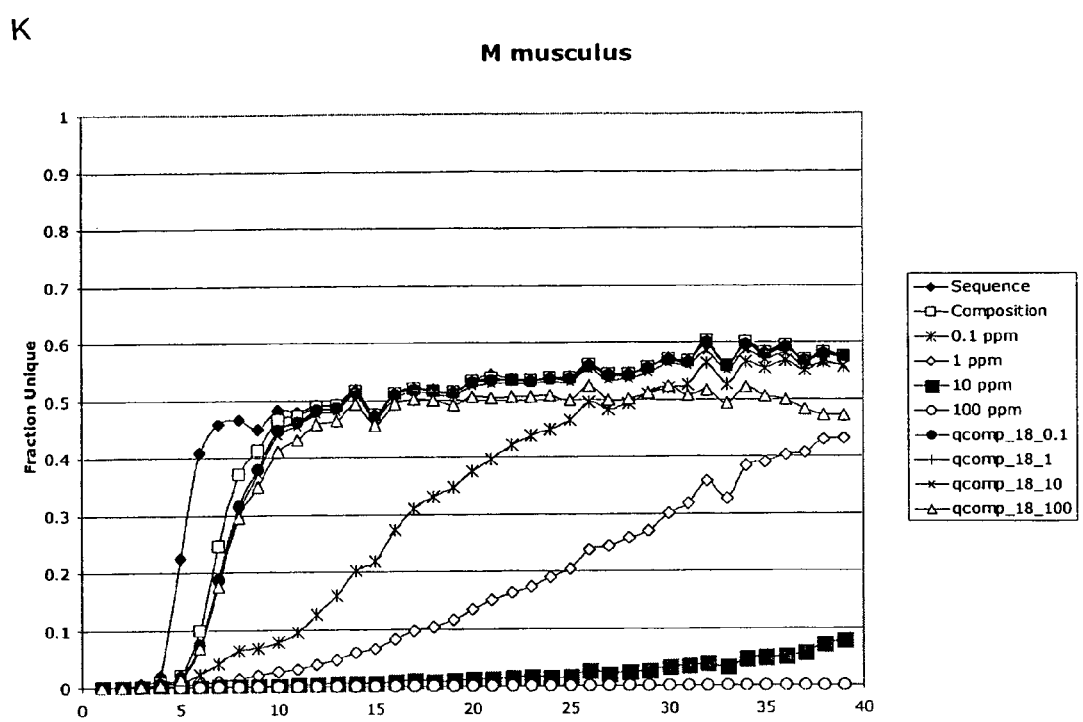

In a preferred embodiment, as the peptides in the predicted peptide database are being generated computationally from an amino acid sequence database, information as to their sequence, protein of origin, and optionally location within the parent protein is also recorded. In addition, a score based on the amino acid composition such as a binary score illustrated in FIG. 1 is also assigned to each predicted peptide. Optionally, a binary score is converted to another type of score such as a decimal score as illustrated in FIG. 1 for easier recognition. The score assigned to a predicted peptide is used to generate a hash table. The key value associated with each member of the hash is the score and a code associated with each member of the hash is a linked list pointer that references an array of peptide information such as the sequence, protein of origin, and location within the parent protein for each peptide that has that score and possible motif for posttranslational modification. This linked list structure allows for the conversion of the amino acid sequence database into an indexed database that can be used to very rapidly identify peptides. Since there are 18 or 19 distinct amino acids in most experiments, a binary score will typically have 18 or 19 bits and can optionally be converted to a value, for example, from 0 to $2^{18}$ (524,288) or from 0 to $2^{19}$ (262,144), as a corresponding decimal score. We estimate that the final number of tryptic peptides derived from the complete, unmodified and finished human proteome will be on the order of $10^6$ peptides and other, less complex genomes will contain fewer peptides. This means that on average, only a few peptides will share the same binary score and the list of peptides associated with each binary score will usually be very short. Validation of this assumption by analysis of the current, nearly complete versions of the yeast and human proteomes are shown in FIGS. 4 and 5. This assumption is also validated for eight other genomes including bacteria, archaea, worm, fly, fish, and rat, as is shown in FIG. 6. It is possible that other genomes still to be sequenced may code for a substantially higher number of peptides, but that will only enhance the efficiency and advantages of the present invention.

Determination of the Identity of a Query Peptide

The qualitative amino acid composition of a query peptide, i.e., the amino acids that are present in the query peptide, is compared to that of the predicted peptides in the predicted peptide database and the identity of the query peptide in terms of its amino acid sequence is determined based on the matched predicted peptides. The mass of the query peptide can optionally be used to confirm or remove a predicted peptide as a matched peptide. The identity of the parent protein of the query peptide may also be determined by tracing a matched predicted peptide to its parent protein.

In one embodiment, the amino acid composition of a query peptide is assigned a binary score and the binary score is compared to the binary scores similarly assigned in the predicted peptide database to identify matched peptides. As illustrated in FIG. 1, the presence or absence of each of the amino acids in a query peptide is recorded in a numerical array. If conditions are used such that every amino acid can be determined, then a full 1×20 array is used. It should be noted that the number of naturally occurring amino acids encoded and incorporated at the time of synthesis of proteins has increased to at least 22, by discovery of means to translate stop codons to insert selenocysteine (Fagegaltier, D. et al. *Embo. J.* 19:4796-805, 2000 and Copeland, P. R. *Gene* 312:17-25, 2003), pyrolysine, or perhaps others to be discovered. These "extra encoded amino acids" are relatively rare occurrences, but may be of high biological importance. The masses of these additional encoded amino acids are unique, as are their fragments, and thus can be identified on a mass spectrum described previously. Given the difficulty in resolving isoleucine from leucine and lysine from glutamine under many experimental conditions, a smaller array, corresponding the number of resolvable amino acids, such as a 1×18 array, can be used for peptide discrimination. This array of ones (the amino acid is observed in either a modified or unmodified form) and zeros (the amino acid is not observed) is a binary number. This binary number (score), or optionally another more easily recognizable number such as a decimal number (score) converted from the binary number, is used to search a predicted peptide database in which the predicted peptides have been indexed with numbers in the same fashion. Peptides with the same number (score) have the same amino acid composition. The search method provided here allows very rapid identification of predicted peptides having the same score as the query peptide.

If the predicted peptide database is properly structured (e.g., a hash table structure), the score for the query peptide can be used as a pointer to access the array of information for the predicted peptides that share the same or nearly the same score. The short list of peptides with similar scores to the query peptide is searched to determine if there is an acceptable match to the parental masses of the query peptide. The parental mass of the query peptide must be adjusted to subtract any modifications that were observed during the initial scan of the immonium ion spectra. Simulations indicate that the above approach can successfully identify the vast majority of peptides and modified peptides.

There are many situations (e.g., where an organism under investigation has not had its genome sequence determined or when the quality of the immonium ion spectrum or other mass spectral information is sub-optimal) in which it is necessary to examine not only exact matches but also close partial matches. In this regard, the acceptable level of tolerance for mismatches (e.g., in terms of Euclidian distance) can be readily determined by a skilled artisan for a particular application. One approach, for example, is to code the stronger immonium ions in more significant digits and the ions with less intensity in the less significant digits of an amino acid composition score. Another approach is to use the data from only the most reliable ions in the immonium ion spectra. This allows for the generation of a series of partial scores, each of which will have much larger peptide lists associated with them. It effect, by shortening the score to just the most reliable data, errors in the less reliable portions of the spectra can be downplayed in part or avoided altogether.

In a situation where no matching peptide is found in a predicted peptide database, the experimentally determined amino acid composition score, i.e., that of the query peptide, is used as a starting point. It is first determined if there is a close peptide mass match in the list of peptide masses associated with that amino acid composition score. If no matches within the specified mass tolerance are found, the search would progress to the first "shell" of amino acid composition scores that differ from the experimental score at one bit position. The peptide masses in these n−1 peptide lists would then be examined for a match of sufficient quality. If no match is found, the search could then be expanded to the further "shells" that encompass amino acid composition scores with 2 or more mismatches. The amino acid composition values for the shells surrounding the experimental amino acid composition can be easily calculated on the fly or, since it is anticipated that for most proteomic databases, only a minor portion of the possible amino acid composition scores will have peptides associated with them, the lists of occupied amino acid composition values surrounding each possible amino acid composition value can be preprocessed and produced at the time that the database is generated, or these lists can be cached each time they are generated. This approach will allow the search to expand so that peptides that mismatch at one or more positions from those present in the database can also be identified. If unique peptides cannot be identified with sufficient accuracy with some types of MS data, the method of the present invention can be used as a prefilter to drastically narrow the range of possible peptides for analysis by slower pairwise comparison or other computationally intensive methods.

If the quality of the mass spectra are good and the amino acid composition score is likely to be reasonably complete and the mass of the query peptide and the amino acid composition score cannot be simultaneously matched then it is likely that undetected post-translational modifications are present. In such cases an iterative process is used starting with the experimental (query) peptide mass. The masses of possible single post-translational modifications are subtracted from the experimental mass and the resulting peptide masses are queried for matching amino acid composition scores. The closest matches are retained and the masses that would result from two, three, or more post-translational modifications are subtracted from the experimental mass and the peptide matches noted. The best matches are noted and the mass spectra are examined for evidence for the possible modifications. The method of the present invention, unlike other peptide identification methods, is rather tolerant of large numbers of simultaneous modifications in peptides since the computations needed to evaluate these possibilities are fast and simple. If the candidate modifications is of interest, targeted MS experiments, or targeted chemical modification and MS experiments can optionally be designed to seek to identify the modifications more definitively. Any peptides that do not yield close matches can be examined by slower pairwise matching methods.

It is to be appreciated that the methods or algorithms of the present invention described herein above may be performed using a computer or processing system which is capable of running application software programs, such as general purpose computer (e.g., a personal computer) or suitable equivalent thereof. For example, a computer can be used to generate a predicted peptide database and to correlate a query peptide to a predicted peptide. It is noted that the predicted peptide database entry for an amino acid composition, a composition score, and other relevant data can be organized into very flexible, complicated structures although they may appear to be a simple text file to a user browser. Preferably, the application program code is embedded in a computer readable medium, such as a floppy disk or computer compact disk. Furthermore, the computer readable medium may be in the form of a hard disk or memory (e.g., random access memory or read only memory) included in the general purpose computer.

As appreciated by one skilled in the art, the computer software code may be written, using any suitable programming language, for example, C or Perl, to configure the computer to perform the methods of the present invention. While it is preferred that a computer program be used to accomplish any of the methods of the present invention, it is similarly contemplated that the computer may be utilized to perform only a certain specific step or task in an overall method, as determined by the user.

The invention will be more fully understood upon consideration of the following non-limiting example.

EXAMPLE

Peptide Identification Using Peptide Amino Acid Attribute Vectors

This example demonstrates that amino acid composition of peptides is virtually as informative as sequence and allows rapid peptide identification more accurately than peptide mass alone. In the peptide identification method provided in this example, peptides are represented as vectors based on composition and grouped into clusters. Unknown peptides are identified by finding the cluster and peptide entry with the shortest Euclidian distance to the unknown peptide.

Materials and Methods

Peptide Amino Acid Composition is Distinctive: We first examined the yeast proteome to explore the usefulness of amino acid composition to uniquely identify peptides from a proteome scale protease digestion. Starting with the non-redundant set of yeast proteins available from The European Bioinformatics Institute (EBI), we performed an in silico trypsin digestion. The resulting peptide sequences were sorted into "bins" according to their sequence and we determined the total number of distinct peptides of a particular. Peptides of unique sequence were identified by noting which of the bins had only one member. Each peptide was converted to an ordered array of amino acids to determine which peptides were unique by composition. Since in mass spectroscopy experiments, amino acids isoleucine (I) and leucine (L) have identical mass and are thus difficult to distinguish and lysine (K) and glutamine (Q) are very close in mass, we also calculated the composition for peptides in which the I and L residues were scored together and the Q and K residues were scored together (Qcomp18). The precise masses of the non-redundant peptides were also calculated and sorted. A peptide was considered to be unique by mass if it was the only peptide within the mass interval for a particular mass resolution.

To determine the fraction of peptides that are unique by different criteria, as shown in FIG. 4, the number unique by sequence, composition, or mass was divided by the total number of peptides of that length. Greater than 95% of peptides 6 amino acids or longer could be uniquely identified from their sequence (FIG. 4, ♦). A maximum of approximately 98% unique peptides by sequence does not change appreciably with increasing peptide length. The reason that this limit does not reach 100% is most likely due to the presence of orthologs and motif sequences present in the database. For amino acid composition, the limit of 98% unique is achieved at a length of 10 amino acids or longer, as shown in FIG. 4 (□), or at a length of 11 amino acids when the composition is based on 18 distinguishable amino acids (FIG. 4, ▲). Thus, for the yeast proteome, a peptide of 11 amino acids or longer can be identified with essentially equal accuracy using either the amino acid sequence or composition. For mass, the 98% unique limit is approached only at a peptide length of 25 with 0.1 ppm mass resolution, as shown in FIG. 4 (◯), and at a peptide length of 40 at 1 ppm mass resolution (FIG. 4, X). A mass resolution of 0.1 ppm is slightly higher than is expected to be experimentally feasible, and a resolution of 1 ppm is achievable by only a few current instruments. Examination of other more or less complex proteomes from human to bacteria yields very similar results to those shown in FIG. 4 (see FIGS. 5 and 6).

As an alternative to pair-wise comparison methods of database searching, we have developed a clustering technique to generate an index to peptide databases, based on Peptide Amino Acid Attribute Vectors (PAAVs). This is accomplished by expressing the peptide composition as an 18 or 20 dimensional set of composition attribute vectors, that are subsequently clustered to form the index. Using PAAV indexed databases, we can rapidly match, and thus identify, a query peptide by performing a limited number of inter-vector distance calculations. This method only requires qualitative composition information (the presence or absence of particular amino acids), can accommodate post-translational modifications and works rather well even with less than complete amino acid composition data. This approach provides a computationally efficient search algorithm that can potentially identify peptides and proteins accurately from MS data in near real time.

Figure 7A:
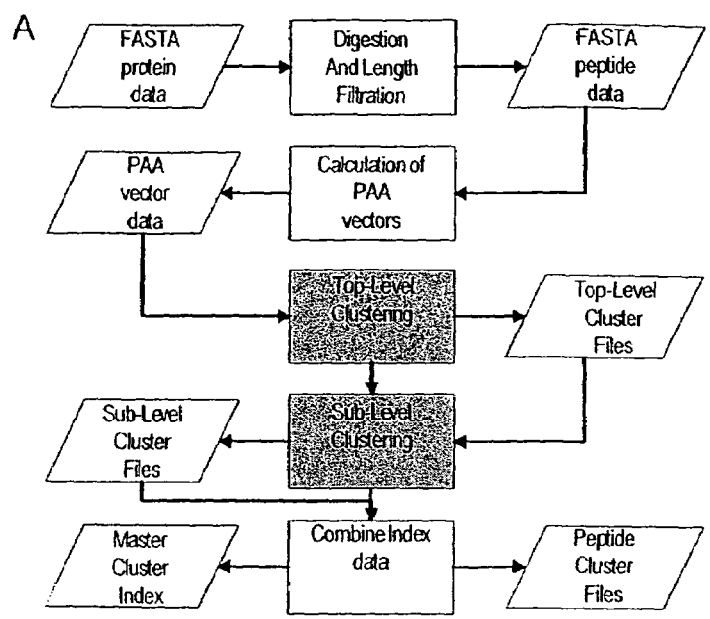
FIG. 7 shows a flowchart of algorithm logic. Panel A: Generation of indexed databases. Shaded areas correspond to clustering algorithm diagramed in Panel B. Panel B: Clustering Algorithm. Panel C: Peptide Identification. Input could either be peptide sequences from theoretical digestion of proteins or peptide compositions from MS/MS de novo peptide composition determinations.
Figure 7B:
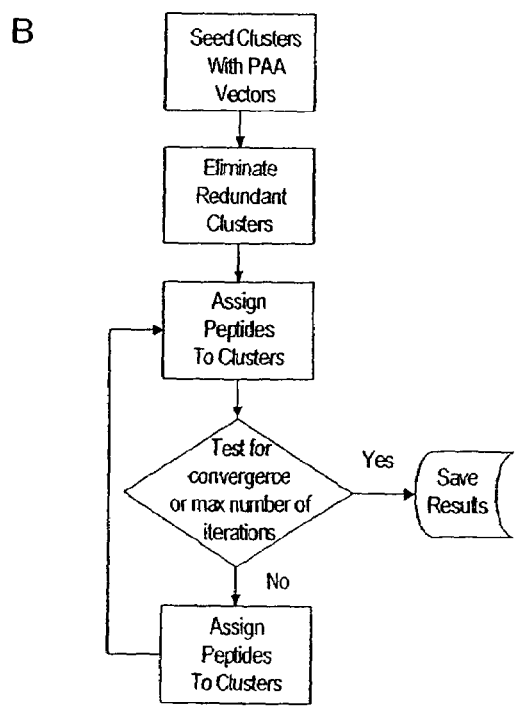
Figure 7C:
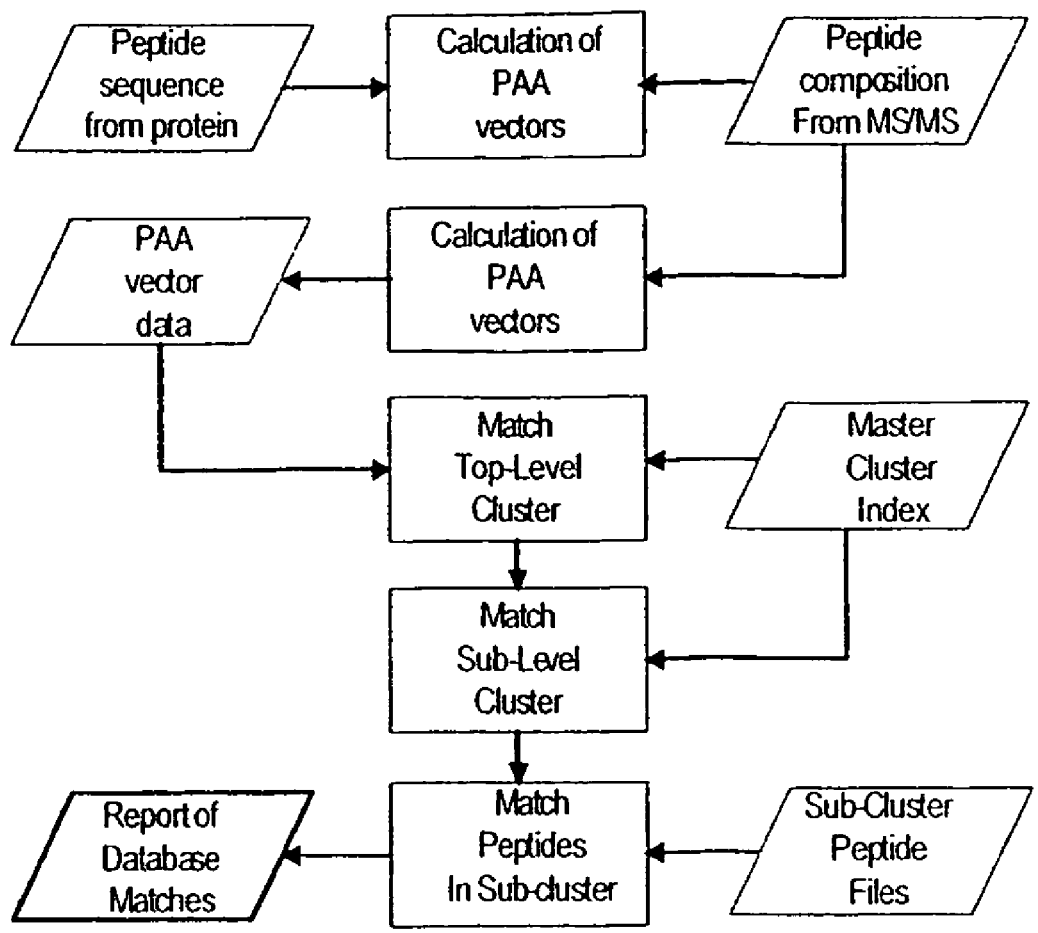
Figure 8:
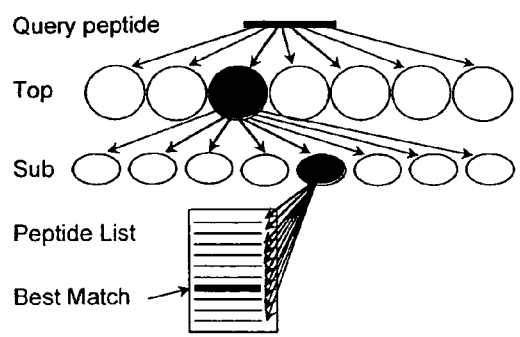
FIG. 8 shows an index cluster tree hierarchy diagram and schematic of the Peptide Amino Acid Attribute Vector (PAAV) peptide identification process.

PAAV Database Construction: Two peptide databases were constructed for this research. The first was derived from the non-redundant yeast (*Saccharomyces cerevisiae*) protein database of from the EBI (September 2003). The second was produced from the mammalian portion of the SwissProt Protein Database (Appel, R. D. et al., *Trends in Biochemical Sciences* 19, 258-260, 1994). A flowchart describing the construction and analysis of the databases is shown in FIG. 7, Panel A and the search index structure is schematically illustrated in FIG. 8.

Figure 9:
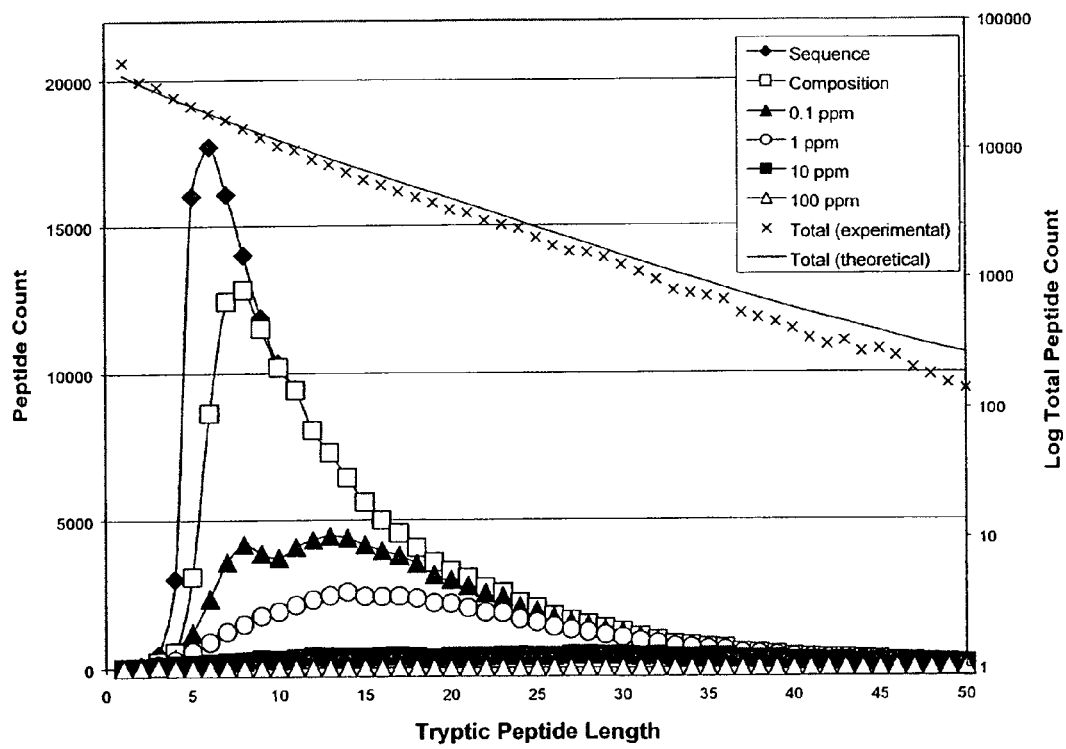
FIG. 9 shows histograms of yeast peptide lengths. The lengths of the theoretical peptides produced in silico from the yeast proteome using the trypsin cleavage specificity α-axis) are plotted vs. the number of peptides of each length (right—log axis). The line represents the expectation of peptide numbers based on the frequency of R and K in the proteome and the total number of peptides. The numbers of peptides that are unique by sequence (♦), composition (□), or mass accuracy (▲, ○, ■, Δ), are plotted on the linear axis (left).

The protein amino acid sequences were processed in silico to produce theoretical tryptic peptides (Keil, B. *Specificity of proteolysis*; Springer-Verlag: New York, 1992). Although any cleavage specificity could be used, trypsin is most commonly used in proteomic experiments. The fraction of peptides of a given length decreases exponentially as peptide length increases as shown in FIG. 9. Since the percentage of unique peptides increases with length (FIG. 4) the number of unique peptides discriminated by each criterion is given by the lower curves in FIG. 9. In proteomics experiments, smaller peptides are typically excluded from analysis and the number of unique peptides is essentially identical for sequence and composition above 11mers. For the SwissProt mammalian database, 389,787 tryptic peptides of 10 or more amino acids were found. Missed enzyme cleavages increase the number of possible peptides, but we show later that a larger number of possible peptides is not a significant impediment to the method and tend to move some of the smaller peptides into a length range that is more useful for identification.

A database of PAAVs is generated in the form of an N×M matrix, where N is the number of entries in the peptide sequence database and M is the number of attributes chosen to describe each member of the peptide sequence database. In this example, 22 or 20 attributes were generated for each peptide. Two of these are text, one formed by combining the protein name and the peptide number and the second, the peptide sequence. The remaining 20 or 18 attributes form the numerical elements of the PAAV for each peptide. The number of each amino acid in a peptide is counted (e.g. the number of alanines) and the amino acid counts are converted to fractional composition by dividing by the total number of amino acids in the peptide. The exponentially distributed frequency values are then mapped to a linear standardized scale, using the following equation:

$$\eta_i = \alpha \ln(v_i=1) - \beta, i=1, \ldots, 20$$

where $\eta_i$ is the standardized value and $v_i$ is the fractional composition of the amino acid in the peptide. The standardization parameters $\alpha$ and $\beta$ are chosen to be $\alpha=6$, $\beta=3$ to provide an appropriate set of vector lengths for use by the clustering algorithm.

PAAV Database Clustering—Clustering Theory: Our goal is to produce an index to the PAAV database that will allow rapid identification of peptides using a relatively small number of simple calculations, as diagrammed in FIG. 8. We have employed data mining techniques to group sets of similar PAAVs into a hierarchal set of clusters. We tested various clustering methods (hierarchical (Eisen, M. B. et al., *Proc. Natl. Acad. Sci. U.S.A.* 95, 14863-14868, 1998), k-means (Hartigan, J. A. *Clustering algorithms*; Wiley: New York, 1975), and self-organizing maps (Kohonen, T. *Self-organizing maps*, 3rd ed.; Springer: New York, 2001)). From these experiments, we have determined that k-means provided the best balance of speed, accuracy and ease of implementation.

In standard k-means clustering, the number of PAAV clusters (k) used to organize the data is selected a priori (Hartigan, J. A. *Clustering algorithms*; Wiley: New York, 1975). Next, k PAAVs are algorithmically or randomly chosen as the centers of the initial k clusters. The Euclidian distance from every PAAV to each of the cluster center vectors is calculated and each PAAV is assigned to the nearest cluster. At the completion of this step, the location of the center of each cluster is re-calculated from the constituent PAAVs. The process is then iterated with newly assigned PAAVs redefining the cluster center vector. Convergence occurs when no changes in PAAV cluster assignment is detected upon further iteration. It is important to note that the clustering process is only required once for each proteome to generate the database PAAV index and is not repeated for each query. This means that the computationally expensive clustering process can be pre-computed and the resulting index used by desktop, laptop or simpler computers to achieve fast peptide identification.

Our initial experiments with clustering of PAAVs demonstrated that there were certain problems with the standard k-means approach. First, it became apparent that a single layer of clusters would not create an effective index and we implemented a second round of clustering, in which the initial set of PAAV clusters were subsequently used for sub-clustering. This allows for the generation of a hierarchical set of clusters allowing the database search to be done using a hierarchical lookup. In the present example, we have used two levels of clusters but in principle, additional cluster levels could be implemented for larger datasets.

A second problem is the difficulty in determining the appropriate number of clusters or sub-clusters that optimally groups the original peptide data. In databases that have a high level of degeneracy, such as the group of all mammalian proteins, top-level clusters may have many copies of identical peptides, primarily from highly homologous or orthologous proteins. To avoid oscillatory problems associated with these "redundant" centers, we have added a step that removes redundant clusters and produces a group of well-distributed cluster centers that converge and are representative of the data.

PAAV Database Clustering—Clustering Algorithm: The algorithm used to generate the indexed peptides database is diagramed in FIG. 7, Panels A & B. The three main steps are: 1) the generation of initial seed clusters, 2) the elimination of redundant clusters, and 3) the iterative assignment of PAAVs to cluster centers. At the start of the process, each peptide is assigned to its own cluster center and therefore the initial number of cluster centers equals the number of input PAAVs. Redundant cluster centers are removed by using a user-defined distance termed the radius of elimination, r. The list of peptides is not altered; only redundant cluster centers within r of each other are removed from the initial cluster center set. All of the PAAVs in the database are assigned to the closest cluster center, new cluster centers are then calculated and the process repeated until no PAAV changes cluster assignment (convergence) or until a user defined number of iterations has been reached. The initial clustering forms the top-level PAAV clusters. The clustering process is then repeated within each cluster, with a smaller radius of elimination, to generate a set of sub-level PAAV clusters. The final product of the clustering is a list of cluster center vectors and a list of PAAVs assigned to each top and sub-level cluster, as diagrammed in FIG. 8.

It often takes more than 100 iterations of PAAV assignments and cluster center recalculations to achieve convergence. Since each of the clusters can be thought of as representing a sphere in 20- or 18-dimensional PAAV space, the structure that we create could be envisioned as a multi-dimensional box (the limits of the extreme values for the PAAVs) containing large spheres (top-level clusters) that each contains smaller spheres (sub-level clusters) that in turn contain individual PAAVs. Each iteration of the clustering algorithm is somewhat analogous to "shaking the box" so that the spheres "settle into position." After a few iterations, the positions of the spheres are nearly settled and little refinement is achieved by additional cycles. In practice, continuing to iterate until no more than 1% of the PAAVs change clusters is sufficient to produce an efficient and accurate index, but saves up to 90% of the computational time of the clustering analysis. The index is pre-computed once for each proteome or combination of possible peptides, speeding up the search for identification of target peptides.

Radius of elimination of Redundant Clusters: The elimination of redundant clusters centers that fall within a fixed distance from each other removes clusters within a "radius of elimination" and allows each PAAV to have a chance to "found" a new cluster. This means that at the point of initial seeding of the clusters, there are a number of clusters equal to the number of vectors that are being clustered. The elimination of redundant clusters has two important ramifications. First, it provides a data driven approach to finding the optimal number and location of the clusters. At the outset, it is impossible to predict what fraction of the 20- or 18-dimensional attribute space that the PAAVs will occupy and whether there will be small pockets of space which are highly occupied and other regions that are sparse, or if the PAAVs will be relatively uniformly distributed throughout the space. This means that an approach like that used in the Kohonen self organizing maps (Kohonen, T. *Self-organizing maps*, 3rd ed.; Springer: New York, 2001), in which a uniform grid of centers is used to seed the clustering, may not accurately describe the set of PAAVs in the database. As the radius of elimination is increased, the number of resulting non-redundant cluster centers decreases exponentially. Experience with larger datasets has shown that as the number of vectors increases, there is only a modest increase in the number of resulting non-redundant clusters. This is likely due to the fact that there are a limited number of cluster centers of a particular radius that fit within the hyperspace described by the PAAVs, or possibly that there are only certain regions of the hyperspace that PAAVs occupy due to physical, evolutionary, or other constraints on their parent peptides.

To better understand the distances between PAAVs in this system, we measured the Euclidian distances between PAAVs for each of the peptides of length 10 amino acids or greater in the yeast proteome from the *Saccharomyces* Genome Database. The average distance between PAAVs was 10.42, with a SD of 1.60. The maximum observed distance was 16.52, which is in agreement with the maximum distance of 16.53 calculated between PAAVs of theoretical peptides of all possible compositions. A distance of less than 0.05 was observed in 4,657 pairs, but in 4,641 of these cases the parent peptides had identical sequences. The remaining 16 cases represented permutations of repeated sequences. Practically, we have found that a value of 10 or 11 for the radius of elimination of the top-level clusters, followed by a value of 5 or 6 for the radius of elimination of the sub-level clusters provides near optimal performance in the construction of databases with a large number of peptides. This allows for a layer of 50 to 120 top-level clusters that each contains 50 to 250 sub-level clusters. This permits a database of hundreds of thousands to millions of peptides to be mapped onto an index structure of a few thousand PAAV clusters.

Peptide Identification Using the PAAV Index: The PAAV indexed peptide database provides a rapid means to locate the best match to a query peptide. The overall approach to the database lookup function is shown in FIG. 7, Panel C and is diagrammed in FIG. 8. The PAAV for the query peptide is determined from the peptide's amino acid composition. The Euclidian distance from that vector to each top-level cluster center is calculated and the query vector is then assigned to the closest top-level cluster. The process is repeated for the corresponding sub-level clusters and the query vector is assigned to a sub-level cluster. Vectors with a Euclidian distance of 0 to the query vector have the same composition and are considered "exact" matches. If no exact match is found, the closest vectors are identified. Using our distance metric, most PAAVs within a distance of 2 are highly related at the sequence level, while those more than 3 apart are unlikely to share sequence similarity.

Results

To test the accuracy of the method, we used the group of rat proteins in the SwissProt database as the query set and two different PAAV databases. This query set consists of 3,216 proteins, which when cleaved in silico using the trypsin specificity and filtered to remove peptides under ten amino acids, yields 55,474 independent peptides. Missed cleavages or loss of ends from tryptic peptides can be accommodated, but for clarity of presentation will not be discussed explicitly. The first database was created using the same proteins used in the query set. This allows us to determine the levels of false negatives (when no exact match to the peptide is found) or false positives (when the peptide is exactly matched to a peptide with a different sequence), as each peptide would be expected to find itself as the best match. In this comparison there were two peptides among the set of 55,474 that were not exactly matched to themselves in the database. These errors appear to occur when the PAAV distance to two different cluster centers is approximately equal and the cluster center assignment then becomes subject to round off errors in the distance calculations. Overall, a 2/55,474 or 0.004% rate of false negative errors was found.

The potential false positives in many cases result from matching peptides from orthologs or redundant protein entries in the sequence database. In a trivial subclass of these cases the peptides match in composition and sequence. A second subclass of cases, are peptides that have the same composition but differ by minor changes, mostly representing orthologs and allelic changes. To distinguish between peptides with identical composition and nearly identical sequences and scoring peptides with identical composition and dissimilar sequences, we used a threshold of 60% direct sequence identity, as would be observed in a 10 amino acid peptide with up to two amino acid exchanges (each exchange losing 20% sequence identity). Peptides with this level of sequence and composition identity are typical of those observed with orthologs and are therefore not likely to be unrelated peptides. This leaves a third class of "anagram" peptides that have identical composition, but have significantly different sequences. There were 21 pairs of these anagram peptides found in the rat database, corresponding to a frequency of 0.04%. An examination of the yeast non-redundant proteome found one misidentified peptide and no anagram peptides. From these results, we conclude that the algorithm is highly accurate in locating peptides in the database.

It is expected that for pair-wise comparison searches such as BLAST or SEQUEST, the length of time for the search will be proportional to o(mn) where n and m are the length of the query and the length of the database, respectively. This implies that the search time will increase linearly with the size of the database being searched. On the other hand, it is expected that an indexed lookup search will not scale linearly, but rather as the number of nodes (n) in the index o(n log(n)) (Andersen, A. and Peterssoni, O. *J. Algorithms* 29, 256-276, 1998). To test this, we repeated the search with the same queries, the full set of rat proteins from the SwissProt database, and compared it to the database generated from the full set of mammalian proteins from the SwissProt database. A search with the same rat protein query set on the database that was approximately seven times larger took less than twice the time. Since it takes 19,123 total clusters to index the rat database and 31,707 total clusters to index the mammalian database, the expected ratio of search times based on the n log(n) ratio would be 1.74, which is very similar to the 1.92 ratio observed for search times of the two databases. If the number of peptides were increased by ten fold while keeping the same cluster structure, even a greater advantage would be gained. It would be expected that the average number of distance measurements would increase from 400 to 520 to accommodate the increase from 12 to 120 peptides on average in each sub cluster, representing 1 distance measurement for 7700 peptides. Thus it would be expected that a ten fold increase in data in the search database would cost 520/400=1.3, or a 30% increase in computational time. This implies that the method would be well suited for very large data sets.

FIG. 9 illustrates the number of unique peptides that can be distinguished in the yeast proteome by each criteria considered. Short peptides inherently cannot be unique in a proteome due to the limited number of different sequence arrangements possible. The number of peptides that are unique by amino acid composition tracks the maximal number of unique peptides above a length of eleven amino acids and is far above the number unique peptides that can be identified by mass, even with a 0.1 ppm mass error.

An important question is how robust this method is, with respect to differences between the query composition and the peptide compositions in the database. This question is important in that differences are expected to arise from noise in the data leading to false positive amino acids calls, missing data leading to false negative amino acid calls, or biological differences between protein homologs, orthologs, or allelic variations leading to changed amino acids. We can model this these types of issues, and determine the effect of amino acid differences on the ability of the method to correctly identify the altered peptides. We chose the *E. Coli* proteome as an example to investigate. To model false positive amino acid calls, we randomly added an amino acid to a peptide used in constructing the database and searched the database with the altered peptide. To model missing amino acids, we randomly deleted an amino acid from the peptide and to model substitutions, as might be caused by biological variation, we randomly removed one amino acid and randomly added one amino acid as a replacement.

Figure 10:
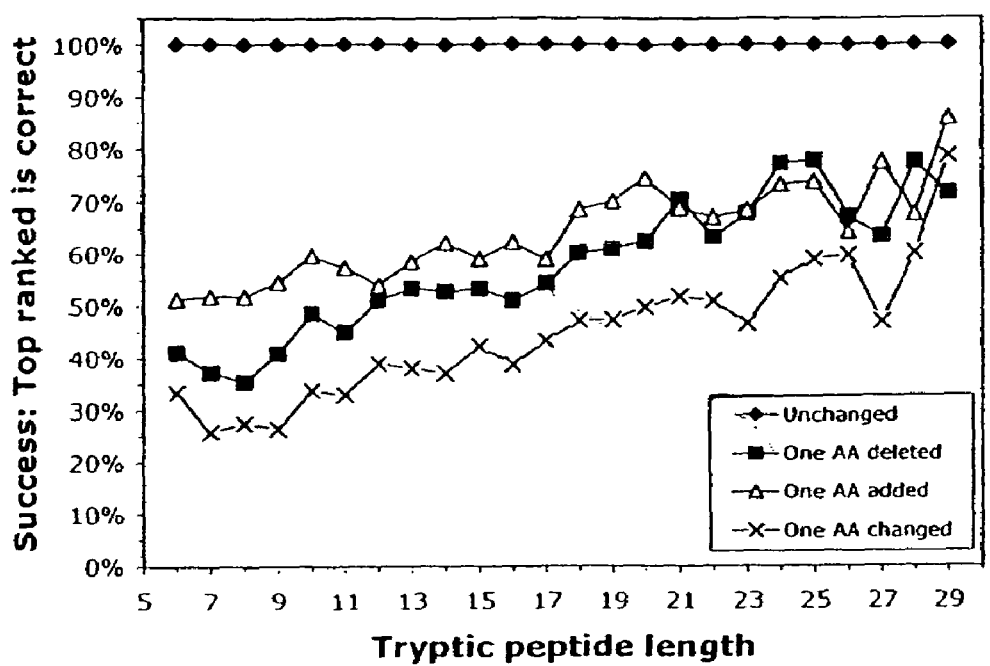
FIG. 10 is a graph of success rates for identifying altered *E. coli* peptides. A clustered database was constructed from the EBI *E. coli* proteome data. Peptides from the database were used to query the database, either in an altered or unaltered form and the frequency of success in peptide identification is graphed vs. the length of the unaltered peptides. Peptides tested were either unchanged (♦), one amino acid was randomly deleted (■), one amino acid was randomly added (Δ), or both one amino acid was randomly deleted and one amino acid was simultaneously randomly added (X). Data are shown for 5,500 peptides tested.

FIG. 10 shows the results of examining 5,500 *E. coli* peptides. For all peptide length, the algorithm successfully identified the unchanged peptide as the best scoring hit in the database 100% of the time. Adding an additional amino acid to the peptide dropped the success rate to approximately 50% for the smallest peptides (fewer than 10 amino acids) while the success rate increases for longer peptides. Deletion of an amino acid had a somewhat greater effect on the success rate and replacement of an amino acid had the greatest impact. The effect of adding multiple amino acids is to lower the success rate, but even with three added amino acids, the success rate is still above 35% for all peptide length. These results demonstrate that this composition-based method is capable of tolerating reasonable amounts of difference between the query and database peptides and therefore the method does not require fully accurate experimental data or complete database.

The present invention is not intended to be limited to the foregoing example, but encompasses all such modifications and variations as come within the scope of the appended claims.

We claim:

1. A method for correlating a query peptide to a protein comprising the steps of:
   providing one or more mass spectra for a query peptide, the query peptide being a protein cleavage product by one or more cleaving agents having defined cleavage specificity, wherein each spectrum comprises masses of members selected from immonium ions, modified immonium ions, fragmented immonium ions, dipeptide ions, fragmented dipeptide ions, tripeptide ions, and fragmented tripeptide ions;
   obtaining a qualitative amino acid composition of the query peptide from said one or more mass spectra, wherein the qualitative amino acid composition indicates the presence or absence of specific amino acids in the peptide, irrespective of the total number of each type of amino acid present;
   comparing the qualitative amino acid composition of the query peptide to a list of qualitative amino acid compositions of a plurality of predicted peptides in a predicted peptide database, the predicted peptides being predicted cleavage products of parent proteins assuming the parent proteins, whose amino acid sequences are known, are subjected to cleavage by said one or more cleaving agents, wherein the comparing step is performed by a computer;
   correlating the query peptide to the parent protein of a predicted peptide whose qualitative amino acid composition is matched to the amino acid composition of the query peptide; and
   outputting to a user the identity of the parent protein to which the query peptide has been correlated.

2. The method of claim 1, wherein the query peptide contains about 9 to about 31 amino acids.

3. The method of claim 1, wherein the cleaving agent is selected from an enzyme and a chemical cleaving agent.

4. The method of claim 1, wherein the cleaving agent is trypsin.

5. The method of claim 1, wherein each predicted peptide is assigned an amino acid composition score which correlates to a unique qualitative amino acid composition.

6. The method of claim 1, wherein the predicted peptide database further comprises a list of qualitative amino acid compositions of predicted peptides that are predicted to be generated when incomplete cleavage of the parent proteins by said one or more cleaving agents occurs.

7. The method of claim 1, wherein the predicted peptide database further comprises a list of molecular masses of the predicted peptides.

8. The method of claim 1, wherein the predicted peptide database is generated by a computer.

9. The method of claim 1, further comprising the step of providing a molecular mass of the query peptide.

10. The method of claim 9, wherein the query peptide is matched to a predicted peptide in the predicted peptide database based on both the qualitative amino acid composition and the molecular mass.

11. The method of claim 10, wherein the molecular mass of the query peptide is adjusted for one or more post-translational modifications.

12. The method of claim 1, wherein the one or more mass spectra are selected from collision induced disassociation spectra and post source decay spectra.

13. The method of claim 1, wherein the one or more mass spectra are generated by matrix assisted laser desorptionlionization (MALDI) or matrix-free surface assisted laser desorptionlionization (SALDI).

14. The method of claim 1, wherein the one or more mass spectra are generated by matrix-free surface assisted laser desorption/ionization (SALDI) using far UV excitation.

15. The method of claim 14, wherein the UV employed is of a wavelength from about 157 nm to about 225 nm.

16. The method of claim 1 further comprising the step of assigning to the query peptide an amino acid composition score that correlates to a unique qualitative amino acid composition.

17. The method of claim 16, wherein the amino acid composition score is a binary score wherein the presence of one particular amino acid residue in the query peptide is represented at a given digit of the binary score by one possible value and the absence of the particular amino acid residue is represented at the given digit of the binary score by the other possible value.

18. The method of claim 16, wherein the query peptide is matched to a predicted peptide having the same or a closely matched amino acid composition score.

19. The method of claim 1, wherein the query peptide is matched to a predicted peptide that differs from the query peptide by one amino acid measured by qualitative amino acid composition.

20. A method for identifying one or more proteins in a sample containing at least one protein, the method comprising the steps of:
   cleaving the protein or proteins in the sample with one or more cleaving agents having defined cleaving specificity to generate query peptides; and
   correlating one or more query peptides to one or more parent proteins according to the method of claim 1 wherein the parent proteins to which the query peptides correlate indicate the identity of the proteins present in the sample.

* * * * *

UNITED STATES PATENT AND TRADEMARK OFFICE
CERTIFICATE OF CORRECTION

PATENT NO.        : 7,603,240 B2
APPLICATION NO.   : 11/038642
DATED             : October 13, 2009
INVENTOR(S)       : Halligan et al.

It is certified that error appears in the above-identified patent and that said Letters Patent is hereby corrected as shown below:

Column 9,   line 3      "sulffidryl" should be --sulfhydryl--

Column 14,  line 46     "$V_i=1$" should be --$V_i+1$--

Column 20,  claim 13    "desorptionlionization" should be --desorption/ionization--

Column 20,  claim 13    "desorptionlionization" should be --desorption/ionization--

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,603,240 B2 Page 1 of 1
APPLICATION NO. : 11/038642
DATED : October 13, 2009
INVENTOR(S) : Brian D. Halligan and Edward A. Dratz It is certified that error appears in the above-identified patent and that said Letters Patent is hereby corrected as shown below:

On the title page, item (73) Assignee, the following should replace the current listing -- The Medical College of Wisconsin, Inc - Milwaukee WI; Montana State University - Bozeman, MT --

Signed and Sealed this
Twenty-first Day of July, 2015

Michelle K. Lee
*Director of the United States Patent and Trademark Office*